United States Patent [19]

Chernesky et al.

[11] Patent Number: 5,475,009
[45] Date of Patent: Dec. 12, 1995

[54] 1,2-DIALKOXYETHANES AS 5-LIPOXYGENASE INHIBITORS

[75] Inventors: Linda J. Chernesky, Arlington Heights; Joseph F. Dellaria, Lindenhurst, both of Ill.

[73] Assignee: Abbott Laboratories, Abbott Park, Ill.

[21] Appl. No.: 304,066

[22] Filed: Sep. 12, 1994

[51] Int. Cl.$^6$ .......................... A61K 31/47; C07D 215/14
[52] U.S. Cl. ............................................. 514/312; 546/157
[58] Field of Search ............................. 514/312; 546/157

[56] References Cited

U.S. PATENT DOCUMENTS

| | | | |
|---|---|---|---|
| 5,217,977 | 6/1993 | Crawley et al. | 514/311 |
| 5,350,754 | 9/1994 | Crawley et al. | 514/277 |
| 5,407,945 | 4/1995 | Bruneau et al. | 514/312 |

Primary Examiner—054753819arren
Assistant Examiner—D. Margaret M. Mach
Attorney, Agent, or Firm—Jerry F. Janssen

[57] ABSTRACT

Compounds of the structure

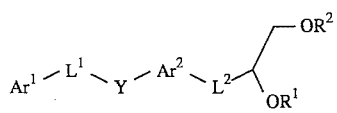

where $Ar^1$ is selected from optionally substituted carbocyclic aryl; optionally substituted 5- or 6-membered heterocyclic aryl; optionally substituted 10-membered bicyclic heterocyclic aryl containing one or two nitrogen atoms; optionally substituted benzo[b]furyl; optionally substituted benzo[b]thienyl;

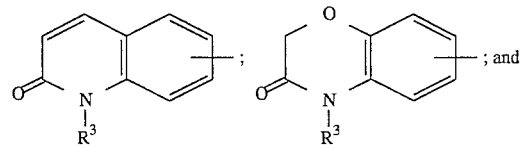

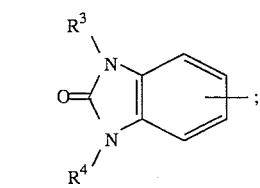

$L^1$ is a valence bond, alkylene, propenylene, or propynylene; Y is oxygen, >NR$^5$, or >S(O)n; $Ar^2$ is optionally substituted phenyl; $L^2$ is

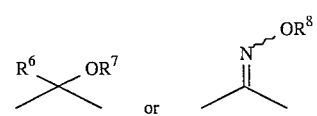

and $R^1$ and $R^2$ are alkyl, or taken together define a group of formula

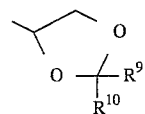

are potent inhibitors of lipoxygenase enzymes and thus inhibit the biosynthesis of leukotrienes. These compounds are useful in the treatment or amelioration of allergic and inflammatory disease states.

7 Claims, No Drawings

1, 2-DIALKOXYETHANES AS 5-LIPOXYGENASE INHIBITORS

TECHNICAL FIELD

This invention relates to compounds having biological activity to inhibit lipoxygenase enzymes, to pharmaceutical compositions comprising these compounds, and to a medical method of treatment. More particularly, this invention concerns certain 1,2-dialkoxyethyl compounds which inhibit leukotriene biosynthesis, to pharmaceutical compositions comprising these compounds and to a method of inhibiting lipoxygenase activity and leukotriene biosynthesis.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis, cis-1,4-pentadiene structures, converting them to 1-hydroperoxy-trans, cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or converted to $LTA_4$. This reactive leukotriene intermediate is enzymatically hydrated to $LTB_4$ or conjugated to the tripeptide glutathione to produce $LTC_4$. $LTA_4$ can also be hydrolyzed nonenzymatically to form two isomers of $LTB_4$. Successive proteolytic cleavage steps convert $LTC_4$ to $LTD_4$ and $LTE_4$. Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the suggestion that they play important roles in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxygenase catalyzes the first step leading to the biosynthesis of all the leukotrienes and therefore inhibition of this enzyme provides an approach to limit the effects of all the products of this pathway. Compounds which inhibit 5-lipoxygenase are thus useful in the treatment of disease states such as those listed above in which the leukotrienes play an important role.

SUMMARY OF THE INVENTION

In its principal embodiment, the present invention provides certain 1,2-dialkoxyethyl compounds which inhibit lipoxygenase enzyme activity and are useful in the treatment of allergic and inflammatory disease states in which leukotrienes play a role.

The compounds of this invention have the structure

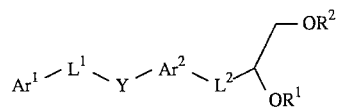

wherein $Ar^1$ is selected from the group consisting of (a) carbocyclic aryl, optionally substituted with alkyl of one to six carbon atoms, haloalkyl of one to six carbon atoms, alkoxy of from one to six carbon atoms, or halogen, (b) 5- or 6-membered heterocyclic aryl, optionally substituted with alkyl of one to six carbon atoms, haloalkyl of one to six carbon atoms, alkoxy of one to six carbon atoms, or halogen, (c) 10-membered bicyclic heterocyclic aryl containing one or two nitrogen atoms, optionally substituted with alkyl of one to six carbon atoms, haloalkyl of one to six carbon atoms, alkoxy of one to six carbon atoms, or halogen, (d) benzo[b]furyl, optionally substituted with alkyl of one to six carbon atoms, haloalkyl of one to six carbon atoms, alkoxy of one to six carbon atoms, or halogen, (e) benzo[b]thienyl, optionally substituted with alkyl of one to six carbon atoms, haloalkyl of one to six carbon atoms, alkoxy of one to six carbon atoms, or halogen, (f)

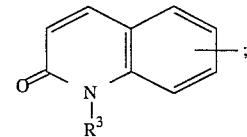

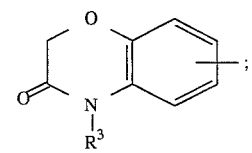

and

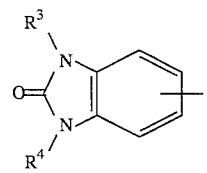

wherein $R^3$ and $R^4$ are independently hydrogen or alkyl of one to four carbon atoms.

$L^1$ is a valence bond or is selected from alkylene of one to three carbon atoms, propenylene, and propynylene, Y is selected from oxygen, $>NR^5$ where $R^5$ is hydrogen or alkyl of one to four carbon atoms, and

where n=0, 1, or 2, and Ar² is phenyl, optionally substituted with one or more substituents selected from alkyl of one to four carbon atoms, alkoxy of one to four carbon atoms, haloalkyl, halogen, cyano, amino, alkoxycarbonyl of one to four carbon atoms, and dialkylaminocarbonyl where the alkyl portions are each independently of one to four carbon atoms.

L² is selected from (a)

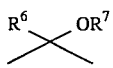

where R⁶ is hydrogen or alkyl of one to four carbon atoms, and R⁷ is alkyl of one to four carbon atoms, and (b)

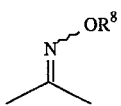

where R⁸ is hydrogen or alkyl of one to four carbon atoms, and R¹ and R² are alkyl of one to four carbon atoms, or taken together with the oxygen atoms to which they are attached, form a ring of the formula

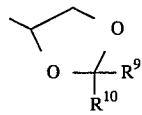

where R⁹ and R¹⁰ are independently selected from hydrogen, alkyl of one to four carbon atoms, alkoxy of one to four carbon atoms, and haloalkyl of one to four carbon atoms.

In another embodiment, the present invention provides pharmaceutical compositions which comprise a therapeutically effective amount of compound as defined above in combination with a pharmaceutically acceptable carrier.

In yet another embodiment, the present invention provides a method of inhibiting leukotriene biosynthesis in a host mammal in need of such treatment comprising administering to a mammal in need of such treatment a therapeutically effective amount of a compound as defined above.

DETAILED DESCRIPTION OF THE INVENTION

Definitions of Terms

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and ten-butyl, and the like.

The term "carbocyclic aryl" denotes a monovalent carbocyclic ring group derived by the removal of a single hydrogen atom from a monocyclic or bicyclic fused or non-fused ring system obeying the "4n+2π electron" or Huckel aromaticity rule. Examples of carbocyclic aryl groups include phenyl, 1-, and 2-naphthyl, biphenyl and the like.

The term "5- or 6-membered heterocyclic aryl" denotes a monovalent heterocyclic ting group derived by the removal of a single hydrogen atom from a monocyclic heterocyclic ring system obeying the "4n+2π electron" or Huckel aromaticity rule. Examples of 5, or 6-membered heterocyclic aryl groups include pyridinyl, furyl, thienyl, thiazolyl, imidazolyl, and pyrimidinyl.

The term "10-membered bicyclic heterocyclic aryl containing one or two nitrogen atoms" refers to a group selected from quinolinyl, isoquinolinyl, quinazolinyl, phthalazinyl, and quinoxalinyl.

The term "propynyl" refers to a straight chain, three-carbon group containing a carbon-carbon triple bond.

The term "hydroxyalkyl" represents an alkyl group, as defined above, substituted by one to three hydroxyl groups with the proviso that no more than one hydroxy group may be attached to a single carbon atom of the alkyl group.

The term "haloalkyl" denotes an alkyl group, as defined above, having one, two, or three halogen atoms attached thereto and is exemplified by such groups as chloromethyl, bromoethyl, trifluoromethyl, and the like.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1 -methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenylene" denotes a divalent group derived from a straight or branched chain hydrocarbon containing at least one carbon-carbon double bond. Examples of alkenylene include —CH=CH—, —CH₂CH=CH—, —C(CH₃)=CH—, —CH₂CH=CHCH₂—, and the like.

By "pharmaceutically acceptable salt" it is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M Berge, et al. describe pharmaceutically acceptable salts in detail in *J. Pharmaceutical Sciences*, 1977, 66: 1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Certain compounds of this invention may exist in either cis or trans or E or Z isomers with respect to the oxime geometry and in addition to stereoisomeric forms by virtue of the presence of one or more chiral centers. The present invention contemplates all such geometric and stereoisomers, including R- and S-enantiomers, diastereomers, and cis/trans or E/Z mixtures thereof as falling within the scope of the invention. If a particular enantiomer is desired, it may be prepared by asymmetric synthesis or by derivatization with a chiral auxiliary and the resulting diastereomeric mixture is separated and the auxiliary group cleaved to provide the pure desired enantiomers.

Preferred Embodiments

Compounds contemplated as falling within the scope of the invention include, but are not limited to:
syn-(4R, 1'R)-2,2-dimethyl-4-[(5-fluoro-3-(napth-2-ylmethyloxy)phenyl)methyloxymethyl]-1,3-dioxolane,
anti-(4R, 1'S)-2,2-dimethyl-4-[(5-fluoro-3-(napth-2-ylmethyloxy)phenyl)methyloxymethyl]-1,3-dioxolane,
anti-(4R, 1'S)-4-[(5-fluoro-3-((napth-2-ylmethyloxy)phenyl)methyloxymethyl]-1,3-dioxolane,
syn-(4R, 1'R)-4-[(5-fluoro-3-(napth-2-ylmethyloxy)phenyl)methyloxymethyl]-1,3-dioxolane, Z-(4S)-O-methyl-2,2-dimethyl-4-[(5-fluoro-3-(napth-2-ylmethyloxy)phenyl)oximinomethyl]-1,3-dioxolane,
E-(4S)-O-methyl-2,2-dimethyl-4-[(5-fluoro-3-(napth-2-ylmethyloxy)phenyl)oximinomethyl]-1,3-dioxolane,
E-(4S)-O-methyl-2,2-dimethyl-4-[(5-fluoro-3-(1,2-dihydro-1-methyl-2-oxoquinoline-6-ylmethyloxy)phenyl)oximinomethyl]-1,3-dioxolane,
Z-(4S)-O-methyl-2,2-dimethyl-4-[(5-fluoro-3-(1,2-dihydro-1-methyl-2-oxoquinoline-6-ylmethyloxy)phenyl)oximinomethyl]-1,3-dioxolane,
anti-(1S, 2R)-1-[(5-fluoro-3-(napth-2-ylmethyloxy)phenyl)]-1,2,3-trimethoxypropane,
syn-(1R,2R)-1-[(5-fluoro-3-(napth-2-ylmethyloxy)phenyl)]-1,2,3-trimethoxypropane,
Z-(1S)-O-methyl-1-[(5-fluoro-3-(napth-2-ylmethyloxy)phenyl)oximinomethyl]-1,2-dimethoxyethane,
E-(1S)-O-methyl-1-[(5-fluoro-3-(napth-2-ylmethyloxy)phenyl)oximinomethyl]-1,2-dimethoxyethane,
anti-(1S, 2R)-1-[(5-fluoro-3-(1,2-dihydro-1-methyl-2-oxoquinoline-6-ylmethyloxy)phenyl)]-1,2,3-trimethoxypropane,
anti-(1S, 2R)-1-methyl-1-[(5-fluoro-3-(1,2-dihydro-1-methyl-2-oxoquinoline-6-ylmethyloxy)phenyl)]-1,2,3-trimethoxypropane,
syn-(1R, 2S)-1-methyl-1-[(5-fluoro-3-(1,2-dihydro-1-methyl-2-oxoquinoline-6-ylmethyloxy)phenyl)]-1,2,3-trimethoxypropane,
E-(4R)-O-methyl-2,2-dimethyl-4-[(5-fluoro-3-(1,2-dihydro-1-methyl-2-oxoquinoline-6-ylmethyloxy)phenyl)oximinomethyl]-1,3-dioxolane,
Z-(4R)O-methyl-2,2-dimethyl-4-[(5-fluoro-3-(1,2-dihydro-1-methyl-2-oxoquinoline-6-ylmethyloxy)phenyl)oximinomethyl]-1,3-dioxolane,
Z-(4R)-O-ethyl-2,2-dimethyl-4-[(5-fluoro-3-(1,2-dihydro-1-methyl-2-oxoquinoline-6-ylmethyloxy)phenyl)oximinomethyl]-1,3-dioxolane,
E-(4R)-O-ethyl-2,2-dimethyl-4-[(5-fluoro-3-(1,2-dihydro-1-methyl-2-oxoquinoline-6-ylmethyloxy)phenyl)oximinomethyl]-1,3-dioxolane,
Z-(4S)-O-ethyl-2,2-dimethyl-4-[(5-fluoro-3-(1,2-dihydro-1-methyl-2-oxoquinoline-6-ylmethyloxy)phenyl)oximinomethyl]-1,3-dioxolane,
E-(4S)-O-ethyl-2,2-dimethyl-4-[(5-fluoro-3-(1,2-dihydro-1-methyl-2-oxoquinoline-6-ylmethyloxy)phenyl)oximinomethyl]-1,3-dioxolane,
Z-(4S)-2,2-dimethyl-4-[(5-fluoro-3-(1,2-dihydro-1-methyl-2-oxoquinoline-6-ylmethyloxy)phenyl)oximinomethyl]-1,3-dioxolane,
E-(4S)-2,2-dimethyl-4-[(5-fluoro-3-(1,2-dihydro-1-methyl-2-oxoquinoline-6-ylmethyloxy)phenyl)oximinomethyl]-1,3-dioxolane,
E-(4S, 2R)-2-methoxy-O-methyl-2,2-dimethyl-4-[(5-fluoro-3-(1,2-dihydro-1-methyl-2-oxoquinoline-6-ylmethyloxy)phenyl)oximinomethyl]-1,3-dioxolane,
E-(4S, 2S)-2-methoxy-O-methyl-2,2-dimethyl-4-[(5-fluoro-3-(1,2-dihydro-1-methyl-2-oxoquinoline-6-ylmethyloxy)phenyl)oximinomethyl]-1,3-dioxolane,
syn-(4R, 1'R)-4-(2,2-dimethyl-((5-fluoro-3-((pyrid-2-yl)prop-1-ynylmethyloxy)phenyl)methyloxymethyl)-1,3-dioxolane,
anti-(4R, 1'S)-4-(2,2-dimethyl-((5-fluoro-3-((pyrid-2-yl)prop-1-ynylmethyloxy)phenyl)methyloxymethyl)-1,3-dioxolane,
Z-(4S)-O-methyl-2,2-dimethyl-4-[(5-fluoro-3-((pyrid-2-yl)prop-1-ynylmethyloxy)phenyl)oximinomethyl]-1,3-dioxolane,
E-(4S)-O-methyl-2,2-dimethyl-4-[(5-fluoro-3-((pyrid-2-yl)prop-1-ynylmethyloxy)phenyl)oximinomethyl]-1,3-dioxolane,
anti-(1S, 2R)-1-[(5-fluoro-3-((pyrid-2-yl)prop-1-ynylmethyloxy)phenyl)]-1,2,3-trimethoxypropane,
syn-(1R, 2R)-1-[(5-fluoro-3-((pyrid-2-yl)prop-1-ynylmethyloxy)phenyl)]-1,2,3-trimethoxypropane,
Z-(1S)-O-methyl-1-[(5-fluoro-3-((pyrid-2-yl)prop-1-ynylmethyloxy)phenyl)oximinomethyl]-1,2-dimethoxyethane,
E-(1S)-O-methyl-1-[(5-fluoro-3-((pyrid-2-yl)prop-1-ynylmethyloxy)phenyl)oximinomethyl]-1,2-dimethoxyethane,
syn-(4R, 1'R)-2,2-dimethyl-4-[(5-fluoro-3-(1,3-dimethyl-2-oxo-2,3-dihydrobenzimidazol-5-ylmethyloxy)phenyl)methyloxymethyl]-1,3-dioxolane,
anti-(4R, 1'S)-2,2-dimethyl-4-[(5-fluoro-3-(1,3-dimethyl-2-oxo-2,3-dihydrobenzimidazol-5-ylmethyloxy)phenyl)methyloxymethyl]-1,3-dioxolane,
Z-(4S)-O-methyl-2,2-dimethyl-4-[(5-fluoro-3-(1,3-dimethyl-2-oxo-2,3-dihydrobenzimidazol-5-ylmethyloxy)phenyl)oximinomethyl]-1,3-dioxolane,
E-(4S)-O-methyl-2,2-dimethyl-4-[(5-fluoro-3-(1,3-dimethyl-2-oxo-2,3-dihydrobenzimidazol-5-ylmethyloxy)phenyl)oximinomethyl]-1,3-dioxolane,
syn-(1R, 2R)-1-[(5-fluoro-3-(1,3-dimethyl-2-oxo-2,3-dihydrobenzimidazol-5-ylmethyloxy)phenyl)]-1,2,3-trimethoxypropane, anti-(1S, 2R)-1-[(5-fluoro-3-(1,3-dimethyl-2-oxo-2,3-dihydrobenzimidazol-5 -ylmethyloxy)phenyl)]-1,2,3-trimethoxypropane,
Z-(1S)-O-Methyl-1-[(5-fluoro-3-(1,3-dimethyl-2-oxo-2,3-dihydrobenzimidazol-5 -ylmethyloxy)phenyl)oximinomethyl]-1,2-dimethoxyethane,
E-(1S)-O-Methyl-1-[(5-fluoro-3-(1,3-dimethyl-2-oxo-2,3-dihydrobenzimidazol-5 -ylmethyloxy)phenyl)oximinomethyl]-1,2-dimethoxyethane,
syn-(4R, 1'R)-2,2-dimethyl-4-[(5-fluoro-3-(napth-2 -ylmethylthio)phenyl)methyloxymethyl]-1,3-dioxolane,
anti-(4R, 1'S)-2,2-dimethyl-4-[(5-fluoro-3-(napth-2 -ylmethylthio)phenyl)methyloxymethyl]-1,3-dioxolane,
syn-(4R, 1'R)-2,2-dimethyl-4-[(5-fluoro-3-(napth-2 -ylmethylsulfinyl)phenyl)methyloxymethyl]-1,3-dioxolane,
anti-(4R, 1'S)-2,2-dimethyl-4-[(5-fluoro-3-(napth-2 -ylmethylsulfinyl)phenyl)methyloxymethyl]-1,3-dioxolane,
syn-(4R, 1'R)-2,2-dimethyl-4-[(5-fluoro-3-(napth-2 -ylmethylsulfonyl)phenyl)methyloxymethyl]-1,3-dioxolane,
anti-(4R, 1'S)-2,2-dimethyl-4-[(5-fluoro-3-(napth-2 -ylmethylsulfonyl)phenyl)methyloxymethyl]-1,3-dioxolane,
Z-(4S )-O-methyl-2,2-dimethyl-4-[(5-fluoro-3-(napth-2 -ylmethylthio)phenyl)oximinomethyl]-1,3-dioxolane,
E-(4S )-O-methyl-2,2-dimethyl-4-[(5-fluoro-3-(napth-2 -ylmethylthio)phenyl)oximinomethyl]-1,3-dioxolane,
syn-(1R, 2R)-1-[(5-fluoro-3-(napth-2-ylmethylthio)phenyl)] -1,2,3 -trimethoxypropane,
anti-(1S, 2R)-1-[(5-fluoro-3-(napth-2-ylmethylthio)phenyl)] -1,2,3 -trimethoxypropane,
Z-(1S)-O-methyl-1-[(5-fluoro-3-(napth-2-ylmethylthio)phenyl)oximinomethyl]-1,2 -dimethoxyethane, and
E-(1S)-O-methyl-1-[(5-fluoro-3-(napth-2-ylmethylthio)phenyl)oximinomethyl]-1,2 -dimethoxyethane.

Preferred compounds are those in which .Ar is selected from the group consisting of (a)naphthyl;

(b)

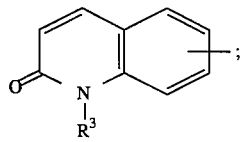

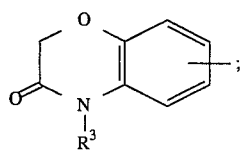

and

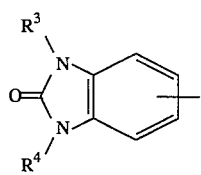

where $R^3$ and $R^4$ are independently hydrogen or alkyl of one to four carbon atoms.

Particularly preferred compounds of the present invention are:
Z-(4S)-O-methyl-2,2-dimethyl-4-[(5-fluoro-3-(napth-2 -ylmethyloxy)phenyl)oximinomethyl]-1,3-dioxolane,
E-(4S)-O-methyl-2,2-dimethyl-4-[(5-fluoro-3-(napth-2 -ylmethyloxy)phenyl)oximinomethyl]-1,3-dioxolane,
E-(4S)-O-methyl-2,2-dimethyl-4-[(5-fluoro-3-(1,2-dihydro-1-methyl-2 -oxoquinoline-6-ylmethyloxy)phenyl)oximinomethyl]-1,3-dioxolane,
Z-(4S)-O-methyl-2,2-dimethyl-4-[(5-fluoro-3-(1,2-dihydro-1-methyl-2 -oxoquinoline-6-ylmethyloxy)phenyl)oximinomethyl]-1,3-dioxolane,
anti-(1S, 2R)-1-[(5-fluoro-3-(napth-2-ylmethyloxy)phenyl)] -1,2,3 -trimethoxypropane,
Z-(1S)-O-methyl-1-[(5-fluoro-3-(napth-2-ylmethyloxy)phenyl)oximinomethyl]-1,2 -dimethoxyethane,
E-(1S)-O-methyl-1-[(5-fluoro-3-(napth-2-ylmethyloxy)phenyl)oximinomethyl]-1,2 -dimethoxyethane,
anti-(1S, 2R)-1-[(5-fluoro-3-(1,2-dihydro-1-methyl-2-oxoquinoline-6 -ylmethyloxy)phenyl))]-1,2,3-trimethoxypropane,
Z-(4S)-O-methyl-2,2-dimethyl-4-[(5-fluoro-3-(napth-2 -ylmethylthio)phenyl)oximinomethyl]-1,3-dioxolane,
E-(4S)-O-methyl-2,2-dimethyl-4-[(5-fluoro-3-(napth-2 -ylmethylthio)phenyl)oximinomethyl]-1,3-dioxolane,
Z-(1S)-O-methyl-1-[(5-fluoro-3-(napth-2-ylmethylthio)phenyl)oximinomethyl]-1,2 -dimethoxyethane,
E-(1S)-O-methyl-1-[(5-fluoro-3-(napth-2-ylmethylthio)phenyl)oximinomethyl]-1,2 -dimethoxyethane,
E-(4R)-O-methyl-2,2-dimethyl-4-[(5-fluoro-3-(1,2-dihydro-1-methyl-2 -oxoquinoline-6-ylmethyloxy)phenyl)oximinomethyl]-1,3-dioxolane,
Z-(4R)-O-methyl-2,2-dimethyl-4-[(5-fluoro-3-(1,2-dihydro-1-methyl-2 -oxoquinoline-6-ylmethyloxy)phenyl)oximinomethyl]-1,3-dioxolane,
Z-(4R)-O-ethyl-2,2-dimethyl-4-[(5-fluoro-3-(1,2-dihydro-1-methyl-2 -oxoquinoline-6-ylmethyloxy)phenyl )oximinomethyl]-1,3-dioxolane, and
E-(4R)-O-ethyl-2,2-dimethyl-4-[(5-fluoro-3-(1,2-dihydro-1-methyl-2 -oxoquinoline-6-ylmethyloxy)phenyl)oximinomethyl]-1,3-dioxolane,
Z-(4S)-O-ethyl-2,2-dimethyl-4-[(5-fluoro-3-(1,2-dihydro-1-methyl-2 -oxoquinoline-6-ylmethyloxy)phenyl)oximinomethyl]-1,3-dioxolane, and
E-(4S)-O-ethyl-2,2-dimethyl-4-[(5-fluoro-3-(1,2-dihydro-1-methyl-2 -oxoquinoline-6-ylmethyloxy)phenyl)oximinomethyl]-1,3-dioxolane.

The most preferred compounds of the present invention are:
Z-(4S)-O-methyl-2,2-dimethyl-4-[(5-fluoro-3-(napth-2 -ylmethyloxy)phenyl)oximinomethyl]-1,3-dioxolane,
E-(4S)-O-methyl-2,2-dimethyl-4-[(5-fluoro-3-(napth-2 -ylmethyloxy)phenyl)oximinomethyl]-1,3-dioxolane,
Z-(4S)-O-methyl-2,2-dimethyl-4-[(5-fluoro-3-(1,2-dihydro-1-methyl-2 -oxoquinoline-6-ylmethyloxy)phenyl)oximinomethyl]-1,3-dioxolane,
E-(4S)-O-methyl-2,2-dimethyl-4-[(5-fluoro-3-(1,2-dihydro-1-methyl-2 -oxoquinoline-6-ylmethyloxy)phenyl)oximinomethyl]-1,3-dioxolane,
Z-(4R)-O-methyl-2,2-dimethyl-4-[(5-fluoro-3-(1,2-dihydro-1-methyl-2 -oxoquinoline-6-ylmethyloxy)phenyl)oximinomethyl]-1,3-dioxolane, and
E-(4R)-O-methyl-2,2-dimethyl-4-[(5-fluoro-3-(1,2-dihydro-1-methyl-2 -oxoquinoline-6-ylmethyloxy)phenyl)oximinomethyl]-1,3-dioxolane.

Lipoxygenase Inhibition Determination

Inhibition of leukotriene biosynthesis was evaluated in an assay, involving calcium ionophore-induced $LTB_4$ biosynthesis expressed human whole blood. Human heparinized whole blood was preincubated with test compounds or vehicle for 15 min at 37° C. followed by calcium ionophore A23187 challenge (final concentration of 8.3 μM) and the reaction terminated after 30 min by adding two volumes of methanol containing prostaglandin $B_2$ as an internal recovery standard. The methanol extract was analyzed for $LTB_4$ using a commercially available radioimmunoassay.

The compounds of this invention inhibit leukotriene biosynthesis as illustrated in Table 1.

TABLE 1

In Vitro Inhibitory Potencies of Compounds of this Invention Against 5-Lipoxygenase from Stimulated $LTB_4$ Formation in Human Whole Blood

| Example | $IC_{50}$ ($10^{-6}$ M) |
| --- | --- |
| 4(Z oxime) | 78% @ 0.78 µM |
| 4(E oxime) | 100% @ 0.20 µM |
| 5 | 95% @ 0.10 µM |
| 6 | 83% @ 0.20 µM |
| 7 | 95% @ 0.20 µM |
| 8 | 92% @ 0.78 µM |
| 9(E oxime) | 28% @ 0.10 µM |
| 10 | 49% @ 0.10 µM |
| 17 | 82% @ 0.78 µM |
| 18 | 96% @ 0.20 µM |
| 19 | 79% @ 1.56 µM |
| 20 | 51% @ 0.10 µM |
| 21 | 100% @ 6.25 µM |
| 22 | 98% @ 0.78 µM |

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carders, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain pan of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and, tragacanth, and mixtures thereof.

Compositions for rectal or vaginal administration are preferably suppositories which can be prepared by mixing the compounds of this invention with suitable nonirritating excipients or carders such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilameliar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology,* Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of the Compounds of the Invention

The compounds of this invention may be prepared by a variety of synthetic routes. Representative procedures are outlined as follows. It should be understood that $Ar^1$, $Ar^2$, $L^1$, $R^1$, $R^6$, and $R^7$, as used herein, correspond to the groups identified above.

The preparation of trialkoxypropane derivatives is shown in Scheme 1. Aryl bromide 1, prepared according to the method described in EPA 385 679, is metallated using, for example, n-butyllithium, in an organic solvent such as THF. Addition of glyceraldehyde acetonide to the aryllithium provides alcohol 2 which is converted to ether 3 by reaction with NaH and $R^7X$, where $R^7$ is alkyl and X is a suitable leaving group such as Cl, Br, I, methanesulfonyl, or p-toluenesulfonyl. Deprotection of the acetonide by treatment with catalytic p-toluenesulfonic acid in methanol affords diol 4 which is converted to trialkoxy compound 5 by reaction with NaH and $R^1X$ where $R^1$ is alkyl and X is defined above. Catalytic hydrogenolysis over Palladium on carbon of 5 affords the intermediate phenol 6. Reaction of 6 with NaH and a compound of formula $Ar^1$-$L^1$-X, where $Ar^1$, $L^1$, and X are defined above, provides 7, which is a representative compound of the invention.

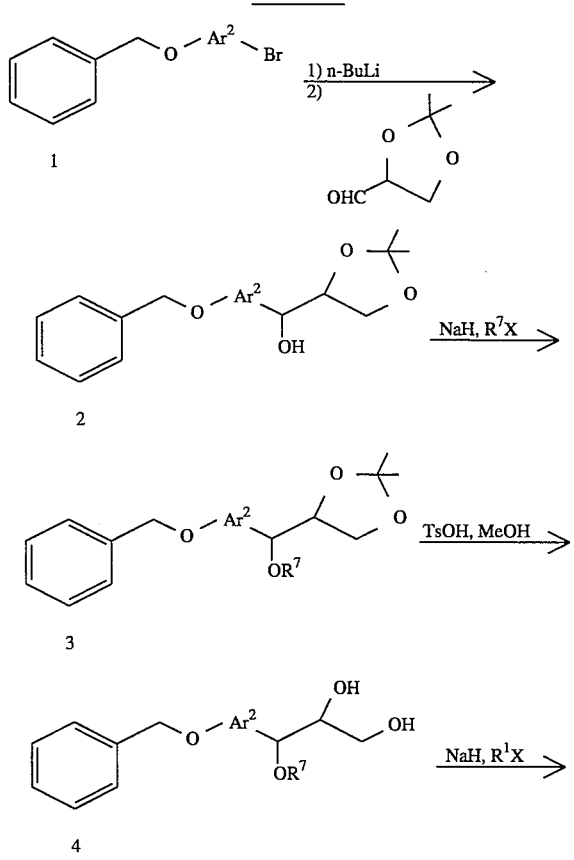

Scheme 1

-continued
Scheme 1

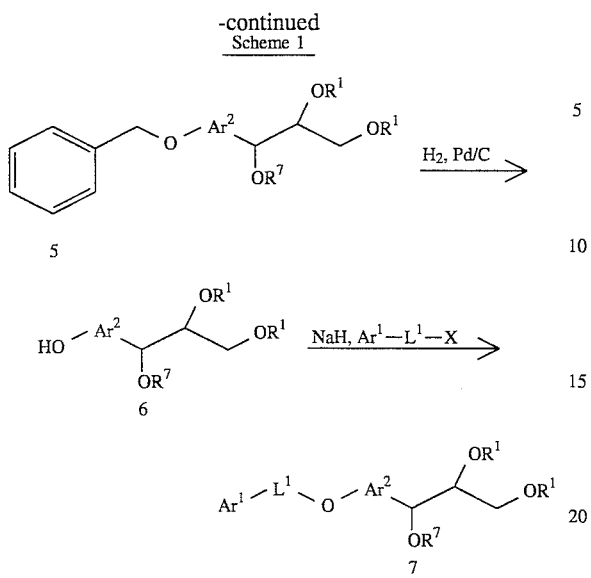

The preparation of dioxolane-containing compounds of the invention is shown in Scheme 2. Diol 4, prepared as shown in Scheme 1, is condensed with carbonyl compound $R^9R^{10}CO$ under standard ketalization conditions to provide 8. The desired compound 9 is then prepared by hydrogenolysis of 8, followed by alkylation of the resulting phenol with $Ar^1-L^1-X$ as described in Scheme 1.

Scheme 2

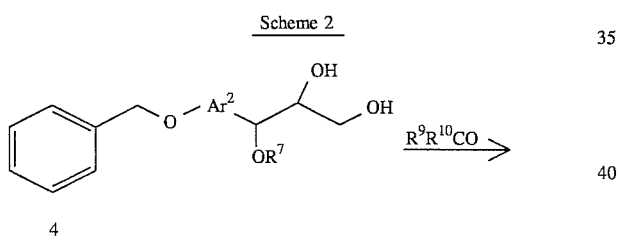

-continued
Scheme 2

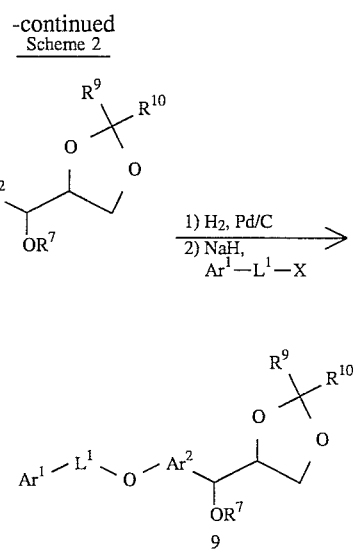

The preparation of oxime-containing compounds of the invention is shown in Scheme 3. Alcohol 2, prepared as in Scheme 1, is oxidized to ketone 10, for example using Swern oxidation conditions (Swern, D., Manusco, A. J., and Huang, S. L., *J. Org. Chem.*, 1978, 43, 2480). Reaction of 10 with $HNOR^8$, where $R^8$ is defined above affords oxime 11. Deprotection of 11 as described in Scheme 1 provides key intermediate 12, which is converted to the desired trialkoxypropane 16 or dioxolane 15 as outlined in Schemes 1 and 2 respectively.

Scheme 3

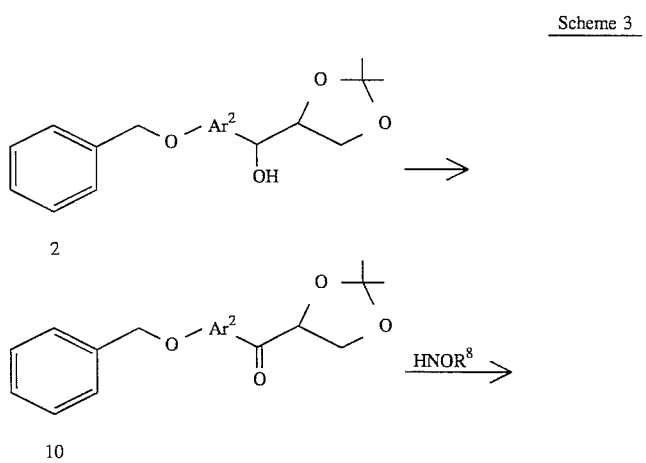

-continued
Scheme 3

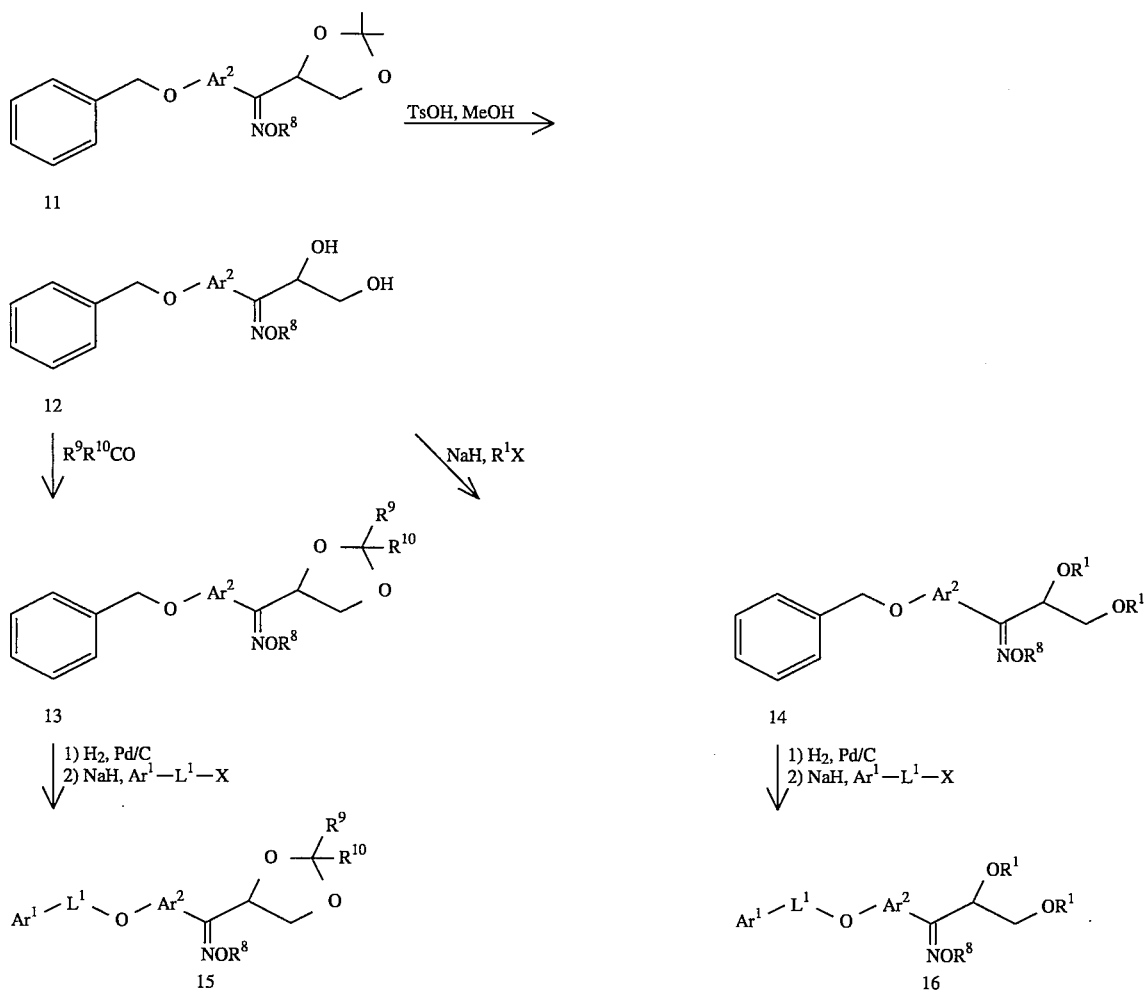

The foregoing may be better understood by the following Examples, which are presented for purposes of illustration and are not intended to limit the scope of the invention.

EXAMPLE 1

Preparation of syn-(4R, 1'R)- and anti-(4R, 1'S)-2,2-dimethyl-4-[(5-fluoro-3 -(napth-2-ylmethyloxy)phenyl)methyloxymethyl]-1,3-dioxolane Step 1: (4R, 1'R)- and (4R, 1'S)-2,2-dimethyl-4-[(5-fluoro-3-(napth-2 -ylmethyloxy)phenylhydroxymethyl]-1,3-dioxolane A flame-dried flask was charged with 3-(napth-2-ylmethyloxy)-5-fluorobromobenzene (0.86 g. 2.6 mmol), prepared according to the method of EPA 385 679, a stir bar, and freshly dried tetrahydrofuran (THF, 23 mL). The resulting solution was cooled to −78° C. under a nitrogen atmosphere and n-butyllithium (2.5M in hexanes, 1.04 mL, 2.6 mmol) was added slowly in a dropwise fashion via syringe. After stirring for 10 minutes at −78° C. a THF solution (6 mL) of (R)-(+)- 2,2-dimethyl-1,3-dioxolane-4-carboxaldehyde (0.34 g, 2.6 mmol), prepared as described in Jackson, *Synthetic Commun.* 1988, 18(4), 337–341) was added. The resulting solution was stirred for 30 minutes at −78° C., and the cooling bath was removed. The reaction was stirred for 1 hour and then quenched with excess saturated aqueous NH₄Cl. The mixture was partitioned between saturated aqueous NH₄Cl and ethyl acetate. The organic layer was washed twice with brine, dried over MgSO₄, filtered, and concentrated in vacuo to provide a cloudy oil which was purified by chromatography on silica gel (20% ether:hexanes) to give the less polar anti-(4R,1'S) alcohol (0.193 g, 20%), a mixture of both isomers (0.233 g, 23%), and the more polar syn-(4R, 1'R) alcohol (0.149 g, 15%).

Step 2: syn-(4R, 1'R)- and anti-(4R, 1'S)-2,2-dimethyl-4-[(5-fluoro-3 -(napth-2-ylmethyloxy)phenyl)methyloxymethyl-1,3-dioxolane Each alcohol isomer prepared is step 1 was independently methylated following the procedure described for the anti-isomer. A flask was charged with anhydrous DMF (5 mL) and(4R, 1'S)-2,2-dimethyl-4-[(5-fluoro-3-(napth-2 -ylmethyloxy)phenyl)hydroxymethyl]-1,3-dioxolane (0.185 g, 0.484 mmol). Sodium hydride (80% oil dispersion, 14.5 mg, 0.484 mmol) was added in a single portion and the reaction mixture was stirred at ambient temperature until gas evolution ceased (5–10 minutes). To the resulting solution was added methyl iodide (103 μL, 0.726 mmol; freshly filtered through a neutral alumina pad) and the reaction mixture was stirred at ambient temperature for 0.5 hours. The reaction was quenched by adding water and was then partitioned between water and ethyl acetate. The organic layer was washed twice with brine, dried over MgSO$_4$, filtered, and concentrated in vacuo to provide a yellow oil which was purified by chromatography on silica gel (50% ether: hexanes) to give anti-(4R, 1'S)-2,2-dimethyl-4-[(5-fluoro-3-(napth-2 -ylmethyloxy)phenyl)methyloxymethyl]-1,3-dioxolane (0.176 g, 92%) as a colorless oil. $^1$H NMR (300 MHz, CDCl$_3$) 6 7.83–7.90 (4H, m), 7.47–7.55 (3H, m), 6.79 (1H, br s), 6.63–6.72 (2H, m), 5.22 (2H, s), ca. 4.12 (1H, m), 4.0–4.05 (3H, 3.35 (3H, s), 1.41 (3H, s), 1.29 (3H, s). MS m/e 397 (M+H)$^+$, 414 (M+NH$_4$)$^{30}$.

Analysis calc'd for C$_{24}$H$_{25}$O$_4$F(0.1 H$_2$O): C, 72.38; H, 6.38. Found: C, 72.14; H, 6.05.

Methylation of (4R, 1'R)-2,2-dimethyl-4-[(5-fluoro-3-(napth-2 -ylmethyloxy)phenyl)hydroxymethyl]-1,3-dioxolane as described above gave syn-(4R, 1'R)-2,2-dimethyl-4-[(5-fluoro-3-(napth-2 -ylmethyloxy)phenyl)methyloxymethyl]-1,3-dioxolane. $^1$H NMR (300 MHz, CDCl$_3$) δ 7.83–7.90 (4H, m), 7.47–7.55 (3H, m), 6.78 (1H, br s), 6.63–6.72 (2H, m), 5.22 (2H, s), 4.24 (1H, quartet, J=7.5 Hz), 4.08 (1H, d, J=7.5 Hz), 3.60 (1H, dd, J= 8.5, 7.5 Hz), 3.52 (1H, dd, J=8.0, 7.5 Hz), 3.25 (3H, s), 1.42 (3H, s), 1.37 (3H, s). MS m/e 397 (M+H)$^+$, 414 (M+NH$_4$)$^+$.

Analysis calc'd for C$_{24}$H$_{25}$O$_4$F(0.75 H$_2$O): C, 70.31; H, 6.15. Found: C, 70.31; H, 5.94.

EXAMPLE 2

Preparation of anti-(4R, 1'S)-4-[(5-fluoro-3-((napth-2 -ylmethyloxy)phenyl)methyloxymethyl]-1,3-dioxlane
Step 1: anti-(1S, 2R)-2,3-dihydroxy-1-methyloxymethyl-1-(5-fluoro-3-(napth-2 -ylmethyloxy)phenyl)propane To a solution of anti-(4R, 1'S)-2,2-dimethyl-4-[(5-fluoro-3-(napth-2 -ylmethyloxy)phenyl)methyloxymethyl]-1,3-dioxolane (0.145 g, 0.37 mmol), prepared as in Example 1, dissolved in methanol (10 mL) was added catalytic para-toluenesulfonic acid monohydrate (25 mg, 0.13 mmol). The reaction was stirred at ambient temperature until TLC indicated complete reaction (~18 hours). The volatiles were removed in vacuo and the resulting solution was partitioned between ethyl acetate and saturated aqueous NaHCO$_3$. The organic phase was washed twice with brine, dried over MgSO$_4$, filtered and concentrated in vacuo to provide anti-(1S, 2R) 2,3-dihydroxy-1-methyloxymethyl-1-(5-fluoro-3-(napth-2 -ylmethyloxy)phenyl)propane as a colorless solid (120 mg, 92%) which was carried on without further purification.
Step 2: anti-(4R, 1'S)-4-[(5-fluoro-3-(napth-2 -ylmethyloxy)phenyl)methyloxymethyl]-1,3-dioxolane To a solution in benzene (100 µL) of anti-(4R, 1'S) 2,3-dihydroxy-1 -methyloxymethyl-1-(5-fluoro-3-(napth-2-ylmethyloxy)phenyl)propane (73 mg, 0.205 mmol), prepared in step 1, were added paraformaldehyde (255 mg, 8.5 mmol) and methanesulfonic acid (3 µL). The reaction mixture was stirred at ambient temperature for 12 hours and concentrated in vacuo. The resulting slurry was partitioned between ethyl ether and water. The organic layer was washed once with saturated aqueous NaHCO$_3$, twice with brine, dried over MgSO$_4$, filtered, and concentrated in vacuo to give a cloudy oil. Purification by column chromatography on silica gel (10% ethyl acetate: hexanes) provided anti-(4R, 1'S)-4-[(5-fluoro-3-(napth-2 -ylmethyloxy)phenyl)methyloxymethyl]-1,3-dioxolane as a cloudy oil (52 mg, 69%). $^1$H NMR (300 MHz, CDCl$_3$) δ 7.83–7.90 (4H, m), 7.48–7.55 (3H, m), 6.80 (1H, br s), 6.65–6.73 (2H, m), 5.22 (2H, s), 5.0 (1H, s), 4.82 (1H, s), 4.03–4.11 m), 3.90–4.00 (2H, m), 3.26 (3H, s). MS m/e 386 (M+H)$^+$.

Analysis calc'd for C$_{22}$H$_{21}$O$_4$F(0.5 H$_2$O): C, 70.01; H, 5.61. Found: C, 70.21; H, 5.58.

EXAMPLE 3

Preparation of syn-(4R, 1'R)-4-[(5-fluoro-3-(napth-2 -ylmethyloxy)phenyl)methyloxymethyl]-1,3-dioxolane The desired compound was prepared according to the method of Example 2, except substituting syn-(4R, 1'R)-2,2-dimethyl-4-[(5-fluoro-3-(napth-2 ylmethyloxy)phenyl)methyloxymethyl]-1,3-dioxolane (0.041 g, 0.12 mmol), prepared as in Example 1 for anti-(4R, 1'S)-2,2-dimethyl-4-[(5-fluoro-3-(napth-2 -ylmethyloxy)phenyl)methyloxymethyl]-1,3-dioxolane provided syn-(4R, 1'R)-4-[(5 -fluoro-3-(napth-2-ylmethyloxy)phenyl)methyloxymethyl]-1,3-dioxolane (25 mg, 59%). $^1$H NMR (300 MHz, CDCl$_3$) δ 7.83–7.90 (4H, m), 7.48–7.55 (3H, m), 6.80 (1H, br s), 6.65–6.73 (2H, m), 5.22 (2H, s), 5.0 (1H, s), 4.82 (1H, s), 4.03– 4.11 (2H, m), 3.90–4.00 (2H, m), 3.26 (3H, s). MS m/e 386 (M+H)$^+$.

Analysis calc'd for C$_{22}$H$_{21}$O$_4$F(0.5 H$_2$O): C, 70.01; H, 5.61. Found: C, 70.21; H, 5.58.

EXAMPLE 4

Preparation of Z- and E-(4S)-O-methyl-2,2-dimethyl-4-[(5-fluoro-3-(napth-2 -yhnethyloxy)phenyl)oximinomethyl]-1,3-dioxolane
Step 1: (4R)-2,2-dimethyl-4-[(5-fluoro-3-(napth-2 -ylmethyloxy)phenyl)carboxymethyl]-1,3-dioxolane Following the Swern oxidation procedure (Swern, D.; Manusco, A. J.; Huang, S. L., *J. Org. Chem.* 1978, 43, 2480) a mixture of (4R, 1'R)- and (4R, 1'S)-2,2-dimethyl-4-[(5-fluoro-3-(napth-2-ylmethyloxy)phenyl)hydroxymethyl]-1,3 -dioxolane (0.55 gm, 1.44 mmol), prepared as in Example 1, step 1, were oxidized to the corresponding ketone (350 mg, 66%) after chromatography on silica gel.
Step 2: Z- and E-(4S)-O-methyl-2,2-dimethyl-4-[(5-fluoro-3-(napth-2 -ylmethyloxy)phenyl)oximinomethyl]-1,3-dioxolane To a solution of (4R)-2,2-dimethyl-4-[(5-fluoro-3-(napth-2 -ylmethyloxy)phenyl)carboxymethyl]-1,3-dioxolane (50 mg, 0.132 mmol), prepared as in step 1, in ethanol (0.5 mL) were added sequentially O-methylhydroxylamine hydrochloride (55 mg, 0.66 mmol) and pyridine (53 µL, 0.66 mmol). The resulting solution was stirred at 40° C. for 1 hour and the volatiles were removed in vacuo. The resulting residue was partitioned between ethyl acetate and water. The aqueous layer was separated and extracted twice with ethyl acetate. The combined organic layers were washed once with saturated aqueous NH$_4$Cl, twice with brine, dried over MgSO$_4$, filtered, and concentrated in vacuo. The isomers were separated by chromatography on silica gel (10% ethyl acetate/hexanes) to give in the order of elution the pure Z-oxime isomer (14.5 mg, 27%), a mixture of both isomers (24.3 mg, 45%), and the pure E-oxime isomer (6.5 mg, 12%). Z-isomer: $^1$H NMR (300 MHz, CDCl$_{3l}$) δ 7.83–7.90 (4H, m), 7.47–7.54 (3H, m), 7.06 (1H, br s), 6.93 (1H, ddd, J=10, 1.5, 2.5 Hz), 6.73 (1H, dt, J=10, 3, 3 Hz), 5.46 (1H, t, J=7 Hz), 5.22 (2H, s), 4.43 (1H, dd, J=7.5, 9 Hz), 3.98 (3H, s), 3.83 (1H, dd, J=9, 7.5 Hz), 1.37 (3H, s), 1.28 (3H, s). MS m/e 410 (M+H)$^+$, 427 (M+NH$_4$)$^+$.

Analysis calc'd for C$_{24}$H$_{24}$NO$_4$F: C, 70.40; H, 5.91; N, 3.42. Found: C, 70.30; H, 5.95; N, 3.43. E-isomer: $^1$H NMR (300 MHz, CDCl$_3$) δ 7.83–7.90 (4H, m), 7.47–7.54 (3H, m), 6.84 (1H, br s), 6.70–6.78 (2H, m), 5.22 (2H, s), 4.85 (1H, t; J= 7.5 Hz), 4.12 (1H, dd, J=7.5, 9 Hz), 3.91 (1H, dd, J=9, 7.5 Hz), 3.84 (3H, s), 1.38 (3H, s), 1.29 (3H, s). MS m/e 410 (M+H)$^+$, 427 (M+NH$_4$)$^+$.

Analysis calc'd for $C_{24}H_{24}NO_4F$: C, 70.40; H, 5.91; N, 3.42. Found: C, 70.30; H, 5.95; N, 3.43.

EXAMPLE 5

Preparation of E-(4S)-O-methyl-2,2-dimethyl-4-[(5-fluoro-3-(1,2-dihydro-1 -methyl-2-oxoquinoline-6-ylmethyloxy)phenyl)oximinomethyl]-1,3-dioxolane Step 1: E-(4S)-O-methyl-2,2-dimethyl-4-[(5-fluoro-3-hydroxyphen-1 -yl)oximinomethyl]-1,3-dioxolane A flask was charged with 10% Pd/C (130 mg) and a solution in ethanol (4.5 mL) of E-(4S)-O- Methyl-2,2-dimethyl-4-[(5-fluoro-3-(napth-2 -ylmethyloxy)phenyl)oximinomethyl]-1,3-dioxolane (450 mg, 1.1 mmol), prepared as in Example 4, was added. The reaction mixture was evacuated and flushed with hydrogen (3 cycles) and maintained under 1 atmosphere of hydrogen at ambient temperature for 1 hour. The reaction mixture was flushed with nitrogen and filtered through a pad of celite. The filter cake was rinsed thoroughly with ethanol and the combined filtrates were concentrated in vacuo. Purification by chromatography on silica gel (10% ethyl acetate/hexanes) gave E-(4S)-O-Methyl-2,2-dimethyl-4-[(5 -fluoro-3-hydroxyphen-1-yl)oximinomethyl]-1,3-dioxolane as a colorless oil (259 mg, 86%).

Step 2: E-(4S)-O-methyl-2,2-dimethyl-4-[(5-fluoro-3-(1,2-dihydro-1-methyl-2 -oxoquinoline-6-ylmethyloxy)phenyl)oximinomethyl]-1,3-dioxolane To a flask containing a solution of E-(4S)-O-Methyl-2,2-dimethyl-4-[(5 -fluoro-3-hydroxyphen-1-yl)oximinomethyl]-1,3-dioxolane (209 mg, 0.93 mmol), prepared as in step 1, in dry DMF (8 mL) was added sodium hydride (80% oil dispersion, 29 mg, 0.97 mmol). After gas evolution ceased 1,2-dihydro-1-methyl-2 -oxoquinolin-6-ylmethylbromide (250 mg, 0.92 mmol) was added in a single portion and the resulting solution was stirred at ambient temperature for 1 hour. The reaction was quenched by the careful addition of water. The resulting solution was partitioned between water and ethyl acetate. The aqueous layer was separated and extracted twice with ethyl acetate. The combined organic layers were washed twice with brine, dried over $MgSO_4$, filtered, and concentrated in vacuo to provide a thick oil. Purification by chromatography on silica gel (5% ethyl acetate/hexanes) provided E-(4 S)-O-methyl- 2,2-dimethyl-4-[(5-fluoro-3-(1,2-dihydro-1-methyl-2-oxoquinoline-6 -ylmethyloxy)phenyl)oximinomethyl]-1,3-dioxolane as a very thick oil (250 mg, 61%). $^1$H NMR (300 MHz, $CDCl_3$) δ 7.68 (1H, d, J=9 Hz), 7.59–7.63 (2H, m), 7.39 (1H, d, J=9 Hz), 6.82 (1H, br s), 6.68–6.77 (2H, m), 5.10 (1H, s), 4.86 (1H, t, J=7.5 Hz), 4.13 (1H, dd, J=8.5, 7.5 Hz), 3.92 (1H, dd, J=8.5, 7.5 Hz), 3.87 (3H, s), 3.74 (3H, s), 1.38 (3H, s), 1.30 (3H, s). MS m/e 441 $(M+H)^+$, 458 $(M+NH_4)^+$.

Analysis calc'd for $C_{24}H_{25}N_2O_5F(0.25 H_2O)$: C, 64.78; H, 5.66; N, 6.30. Found: C, 64.89; H, 5.61; N, 6.30.

EXAMPLE 6

Preparation of Z-(4S)-O-methyl-2,2-dimethyl-4-[(5-fluoro-3-(1,2-dihydro-1-methyl- 2-oxoquinoline-6-ylmethyloxy)phenyl)oximinomethyl]-1,3-dioxolane The desired compound was prepared according to the procedure described in example 5 except substituting Z-(4S)-O-Methyl-2,2-dimethyl-4-[(5-fluoro-3-(napth- 2-yl-)methoxyphenyl)oximinomethyl]-1,3-dioxolane, prepared as in Example 4, for E-( 4S)-O-Methyl-2,2-dimethyl-4-[(5-fluoro-3-(napth-2 -ylmethyloxy)phenyl)oximinomethyl]-1,3-dioxolane. Purification by chromatography on silica gel (40% ethyl acetate/hexanes) provided the title compound as a very thick oil (86%). $^1$H NMR (300 MHz, $CDCl_3$) δ 7.69 (1H, d, J=9 Hz), 7.59–7.63 (2H, m), 7.39 (1H, d, J=9 Hz), 7.02 (1H, br s), 6.95 (1H, ddd, J=9.5, 1.5, 2 Hz), 6.68–6.77 (2H, m), 5.46 (1H, t, J=7.5 Hz), 5.12 (2H, s), 4.44 (1H, dd, J=8.5, 7.5 Hz), 3.97 (3H, s), 3.84 (1H, dd, J=8.5, 7.5 Hz), 3.74 (3H, s), 1.38 (3H, s), 1.30 (3H, s) ; MS m/e 441 $(M+H)^+$, 458 $(M+NH_4)^+$.

Analysis calc'd for $C_{24}H_{25}N_2O_5F$: C, 65.45; H, 5.72; N, 6.36. Found: C, 65.50; H, 5.49; N, 6.16.

EXAMPLE 7

Preparation of anti-(1S, 2R)-1-(5-fluoro-3-(napth-2-ylmethyloxy)phenyl)]-1,2,3 -trimethoxypropane To a solution in dry THF (5 mL) of anti-(1S, 2R)-2,3-dihydroxy-1-[(5 fluoro-3-(napth-2-ylmethyloxy)phenyl)]-1-methoxypropane (50 mg, 0.14 mmol), prepared as in Example 2, step 1, was added sodium hydride (8.4 mg; 80% oil dispersion; 0.28 mmol) was. After gas evolution ceased, methyl iodide (17 μL; 0.28 mmol) was added and the reaction was stirred at ambient temperature for 15 hours. Excess sodium hydride was quenched by careful addition of water. The reaction was partitioned between water and ethyl acetate. The aqueous layer was extracted twice with ethyl acetate. The combined organic layers were washed with brine, dried over $MgSO_4$, filtered, and concentrated in vacuo to provide an orange oil. Purification by silica gel chroatography (ethyl acetate/hexanes) provided pure anti-(1S, 2R)-1-[(5 -fluoro-3-((napth-2-yl)methoxy)-phenyl)]-1,2,3-trimethoxypropane (40 mg, 74% ). $^1$H NMR (300 MHz, $CDCl_3$) δ 7.83–7.90 (4H, m), 7.47–7.55 (3H, m), 6.82 (1H, br s), 6.65–6.72 (2H, m) , 5.22 (2H, s), 4.21 (1H, d, J=6 Hz), 3.47–3.53 (2H, m), 3.34–3.42 (1H, m), 3.34 (3H, s), 3.27 (3H, s), 3.25 (3H, s). MS m/e 402 $(M+NH_4)^+$.

Analysis calc'd for $C_{23}H_{25}O_4F$: C, 71.86; H, 6.55. Found: C, 71.61; H, 6.52.

EXAMPLE 8

Preparation of syn-(1R, 2R)-1-[(5-fluoro-3-(napth-2-ylmethyloxy)phenyl)]-1,2,3 -trimethoxypropane Step 1: syn-(1R, 2R)-2,3-dihydroxy-1-[(5-fluoro-3-(napth-2-ylmethyloxy)phenyl)] -1 -methoxypropane The desired compound was prepared and carried on without further purification according to the method of Example 2, step 1, except substituting (4R, 1'R)-2,2-dimethyl-4-[(5-fluoro-3-(napth-2-ylmethyloxy)phenyl)methyloxymethyl] -1,3-dioxolane (80 mg, 0.20 mmol), prepared as in Example 1, step 2, for (4R, 1'S)- 2,2-dimethyl-4-[(5-fluoro-3-(napth-2-ylmethyloxy)phenyl)methyloxymethyl]-1,3-dioxolane.

Step 2: syn-(1R, 2R)-1-[(5-fluoro-3-(napth-2-ylmethyloxy)phenyl)]-1,2,3 -trimethoxypropane The desired compound was prepared according to the method of Example 7, except substituting syn-(1R, 2R)-2, 3-dihydroxy-1-[(5-fluoro-3-(napth-2 -ylmethyloxy)phenyl)] -1-methoxypropane (50 mg, 0. 14 mmol), prepared in step 1, for anti-(1S, 2R)-2,3-dihydroxy-1-[(5-fluoro-3-(napth-2-yl-methyloxy)phenyl))]-1 -methoxypropane. $^1$H NMR (300 MHz, $CDCl_3$) δ 7.83–7.90 (4H, m), 7.47–7.55 (3H, m), 6.82 (1H, br s), 6.65–6.72 (2H, m), 5.22 (2H, s), 4.28 (1H, d, J= 6 Hz), 3.35–3.48 (2H, m), 3.07 (1H, dd, J=9, 4.5 Hz), 3.42 (3H, s), 3.27 (3H, s), 3.25 (3H, s). MS m/e 402 $(M+NH_4)^+$.

Analysis calc'd for $C_{23}H_{25}O_4F(0.25 H_2O)$: C, 71.03; H, 6.48. Found: C, 71.00; H, 6.36.

EXAMPLE 9

Preparation of Z- and E-(1S)-O-methyl-1-[(5-fluoro-3-(napth-2 -ylmethyloxy)phenyl)oximinomethyl]-1,2-dimethoxyethane Step 1: E- and Z-((1S)-O-methyl-1-[(5-fluoro-3-(napth-2-ylmethyloxy)phenyl)oximinomethyl]-1,2-dihydroxyethane The desired compounds were prepared according to the method of Example 2, step 1, except substituting a 1:1 mixture of Z- and E-(4S)-O-methyl-2,2-dimethyl-4 -[(5-fluoro-3-(napth-2-ylmethyloxy)phenyl)oximinomethyl]-1, 3-dioxolane, prepared as in Example 4, for anti-(4R, 1'S)-2,2-dimethyl-4-[(5-fluoro-3-(napth-2 -ylmethyloxy)phenyl) methyloxymethyl]-1,3-dioxolane.

Step 2: Preparation of Z- and E-(1S)-O-methyl-1-[(5-fluoro-3-(napth-2 -ylmethyloxy)phenyl)oximinomethyl]-1,2-dimethoxyethane The desired compounds were prepared according to the method of Example 7, except substituting E- and Z-(4R)-O-methyl-1-[(5-fluoro-3-(napth-2 -ylmethyloxy)phenyl)oximinomethyl]-1,2-dihydroxyethane (105 mg, 0.29 mmol), prepared as in step 1, for anti-(1S, 2R)-2,3-dihydroxy-1-[(5-fluoro-3-(napth-2 -ylmethyloxy)phenyl)]-1-methoxypropane. Separation of the geometrical isomers by chromatography on silica gel (10% ethyl acetate/hexanes) provided in the order of elution the Z-isomer (25 mg, 22%), E-isomer (21 mg, 19%), and a 1:1 mixture of the corresponding E- and Z-monomethylatedoximes (24 mg, 22%). Z-isomer: $^1$H NMR (300 MHz, CDCl$_3$) δ 7.80–7.90 (4H, m), 7.47–7.54 (3H, m), 7.28 (1H, br s), 7.12 (1H, ddd, J=10, 1.5, 2.5 Hz), 6.74 (1H, dt, J=10, 3, 3 Hz), 5.22 (2H, s), 5.08 (1H, dd, J=7, 3 Hz), 3.99 (3H, s), 3.71 (1H, dd, J=10.5, 7.5 Hz), 3.50 (1H, dd, J=10.5, 3.5 Hz), 3.38 (3H, s), 3.27 (3H, s). MS m/e 398 (M+H)$^+$, 415 (M+NH$_4$)$^+$.

Analysis calc'd for C$_{23}$H$_{24}$NO$_4$F(0.25 H$_2$O): C, 68.73; H, 6.02; N, 3.48. Found: C, 68.39; H, 6.09; N, 3.30. E-isomer: $^1$H NMR (300 MHz, CDCl$_3$) δ 7.82–7.90 (4H, m), 7.47–7.54 (3H, m), 6.84 (1H, br s), 6.70–6.78 (2H, m), 5.21 (2H, s), 4.15 (1H, dd, J=7, 6 Hz), 3.87 (3H, s), 3.47 (3H, s), 3.40–3.47 (1H; m), 3.27–3.32 (1H, m), 3.27 (3H, s). MS m/e 398 (M+H)$^+$, 415 (M+NH$_4$)$^+$.

Analysis calc'd for C$_{23}$H$_{24}$NO$_4$F(0.25 H$_2$O): C, 68.73; H, 6.02; N, 3.48. Found: C, 68.39; H, 6.09; N, 3.30.

EXAMPLE 10

Preparation of anti-(1S, 2R)-1-[(5-fluoro-3-(1,2-dihydro-1-methyl-2-oxoquinoline-6 -ylmethyloxy)phenyl)]-1,2,3-trimethoxypropane The desired compound was prepared according to the method of Example 5, except substituting anti-(1S, 2R)-1-[(5-fluoro-3-(napth-2-ylmethyloxy)phenyl)] -1,2,3-trimethoxypropane, prepared as in Example 7, for E-(4S)-O-Methyl-2,2 -dimethyl-4- [(5-fluoro-3-(napth-2-ylmethyloxy)phenyl)oximinomethyl]-1,3 -dioxolane. $^1$H NMR (300 MHz, CDCl$_3$) δ 7.61–7.71 (3H, m), 7.39 (1H, d, J=9 Hz), 6.81 (1H, br s), 6.73 (1H, d, J=9.5 Hz), 6.72 (1H, br d, J=9.5 Hz), 6.63 (1H, dt, J=10.5, 3 Hz), 5.12 (2H, s), 4.21 (1H, d, J=6 Hz), 3.74 (3H, s), 3.48– 3.52 (2H, m), 3.36–3.42 (1H, m), 3.36 (3H, s), 3.27 (3H, s), 3.25 (3H, s). MS m/e 416 (M+H)$^+$, 433 (M+NH$_4$)$^+$.

Analysis calc'd for C$_{23}$H$_{26}$NO$_5$F: C, 66.49; H, 6.3 1; N, 3.37. Found: C, 66.24; H, 6.54; N, 3.25.

EXAMPLE 11

Preparation of syn-(4R, 1'R)- and anti-(4R, 1'S)-2,2-dimethyl-4-[(5-fluoro-3 -(napth- 2-ylmethylthio)phenyl)methyloxymethyl]-1,3-dioxolane Step 1: (4R, 1'R)- and (4R, 1'S)-2,2-dimethyl-4-(5-fluoro-3 -(benzylthio)phenyl)methyloxymethyl]-1,3-dioxolane The desired compounds are prepared according to the method of Example 1, steps 1 and 2, except substituting 5-fluoro-3-benzylthiobromobenzene, prepared as described in EPA 420 511 (Example 4), for 3-(napth-2-ylmethyloxy)-5-fluorobromobenzene.

Step 2: (4R, 1'R)- and (4R, 1'S)-2,2-dimethyl-4-[(5-fluoro-3 -mercaptophenyl)methyloxymethyl]-1,3-dioxolane The desired compounds are prepared by debenzylation of (4R, 1'R)- and (4R, 1'S)-2,2-dimethyl-4-[(5-fluoro-3-benzylthiophenyl)methyloxymethyl]-1,3-dioxolane, prepared in step 1, with benzoyl peroxide as described in EPA 420 511 (Example 4).

Step 3: syn-(4R, 1'R)- and anti-(4R, 1'S)-2,2-dimethyl-4-[(5-fluoro-3 -(napth-2-ylmethylthio)phenyl)methyloxymethyl]-1,3-dioxolane The desired compounds are prepared according to the method of Example 5, step 2, except substituting (4R, 1'R)- and (4R, 1'S)-2,2-dimethyl-4- [(5-fluoro-3-mercaptophenyl)methyloxymethyl]-1,3-dioxolane, prepared as in step 2, for E-(4R)-O-Methyl- 2,2-dimethyl-4-[(5-fluoro-3-hydroxyphen-1-yl)oximinomethyl]-1,3 -dioxolane, and 2-bromomethylnaphthylene for 1,2-dihydro-1-methyl-2-oxoquinolin-6-methylbromide.

EXAMPLE 12

Preparation of syn-(4R, 1'R)- and anti-(4R, 1'S)-2,2-dimethyl-4-[(5-fluoro-3 -(napth-2-ylmethylsulfinyl)phenyl)methyloxymethyl]-1,3-dioxolane The desired compounds are prepared by oxidation of syn-(4R, 1'R)- and anti-( 4R, 1'S)-2,2-dimethyl-4-[(5-fluoro-3-(napth-2 -ylmethylthio)phenyl)methyloxymethyl]-1,3-dioxolane, prepared as in Example 11, with sodium metaperiodate as described in EPA 409 413 (Example 7).

EXAMPLE 13

Preparation of syn-(4R, 1'R)- and anti-(4R, 1'S)-2,2-dimethyl-4-[(5-fluoro-3 -(napth-2-ylmethylsulfonyl)phenyl)methyloxymethyl]-1,3-dioxolane The desired compounds are prepared by oxidation of syn-(4R, 1'R)- and anti-( 4R, 1'S)-2,2-dimethyl-4-[(5-fluoro-3-(napth-2 -ylmethylthio)phenyl)methyloxymethyl]-1,3-dioxolane, prepared as in Example 11, with potassium peroxymonosulfate as described in EPA 409 413 (Example 14).

EXAMPLE 14

Preparation of Z- and E-(4S)-O-methyl-2,2-dimethyl-4-[(5-fluoro-3 -(napth-2-ylmethylthio)phenyl)oximinomethyl]-1, 3-dioxolane Step 1: Z- and E-(4S)-O-methyl-2,2-dimethyl-4-[(5-fluoro-3 -benzylthiophenyl)oximinomethyl]-1,3-dioxolane The desired compounds are prepared according to the method of Example 4, steps 1 and 2, except substituting a mixture of (4R, 1'R)- and (4R, 1'S)-2,2 -dimethyl-4-[(5-fluoro-3-benzylthiophenyl)hydroxymethyl]-1,3-dioxolane, prepared as in Example 11, step 1, for a mixture of (4R, 1'R)- and (4R, 1'S)-2,2-dimethyl-4 -[(5-fluoro-3-(napth-2-ylmethyloxy)phenyl)hydroxymethyl]-1,3-dioxolane.

Step 2: Z- and E-(4S)-O-methyl-2,2-dimethyl-4-[(5-fluoro-3-(napth-2 -ylmethylthio)phenyl)oximinomethyl]-1,3-dioxolane The desired compounds are prepared according to the method of Example 11, steps 2 and 3, except substituting a mixture of Z- and E-(4S)-O-methyl-2,2-dimethyl- 4-[(5-fluoro-3-benzylthiophenyl)oximinomethyl]-1,3-dioxolane, prepared as in step 1, for (4R, 1'R)- and (4R, 1'S)-2,2-dimethyl-4-[(5-fluoro-3 -benzylthiophenyl)methyloxymethyl]-1,3-dioxolane.

EXAMPLE 15

Preparation of syn-(1R, 2R) and anti-(1S, 2R)-1-[(5-fluoro-3-(napth-2 -ylmethylthio)phenyl)]-1,2,3-trimethoxypropane Step 1: syn-(1R,2R) and anti-(1S, 2R)-1-(5-fluoro-3-benzylthiophenyl)-1,2,3 -trimethoxypropane The desired compounds are prepared according m the method of Example 8, except substituting a mixture of (4R, 1'R)- and (4R, 1'S)-2,2-dimethyl-4-[(5-fluoro- 3-(benzylthio)phenyl)methyloxymethyl]-1,3-dioxolane, prepared as in Example 11, step 1, for (4R, 1'R)-2,2-dimethyl-4-[(5-fluoro-3-(napth-2 -ylmethyloxy)phenyl)methyloxymethyl]-1,3-dioxolane.

Step 2: syn-(1R, 2R) and anti-(1S, 2R)-1-[(5-fluoro-3-(napth-2 -ylmethylthio)phenyl)]-1,2,3-trimethoxypropane The desired compounds are prepared according to the method of Example 11, steps 2 and 3, except substituting a mixture of syn-(1R,2R) and anti-(1S, 2R)-1-(5 -fluoro-3-benzylthiophenyl)-1,2,3-trimethoxypropane, prepared as in step 1, for (4R, 1'R)- and (4R, 1'S)-2,2-dimethyl-4-[(5-fluoro-3 -benzylthiophenyl)methyloxymethyl]-1,3-dioxolane.

EXAMPLE 16

Preparation of Z- and E-(1S)-O-Methyl-1-[(5-fluoro-3-(napth-2 -ylmethylthio)phenyl)oximinomethyl]-1,2-dimethoxyethane Step 1: Z- and E-(4R)-O-Methyl-1-[(5-fluoro-3-benzylthiophenyl)oximinomethyl] -1,2-dimethoxyethane The desired compounds are prepared according to the method of Example 9, steps 1 and 2, except substituting Z- and E-(4S)-O-methyl-2,2-dimethyl-4-[(5-fluoro- 3-benzylthiophenyl)oximinomethyl]-1,3-dioxolane, prepared as in Example 14, step 1, for Z- and E-(4S)-O-methyl-2,2-dimethyl-4-[(5-fluoro-3-(napth-2 -ylmethyloxy)phenyl)oximinomethyl]-1,3-dioxolane.

Step 2: Z- and E-(4S)-O-Methyl-1-[(5-fluoro-3-(napth-2 -ylmethylthio)phenyl)oximinomethyl]-1,2-dimethoxyethane The desired compounds are prepared according to the method of Example 11, steps 2 and 3, except substituting a mixture of Z- and E-(4S)-O-Methyl-1-[(5-fluoro- 3-benzylthiophenyl)oximinomethyl]-1,2-dimethoxyethane, prepared as in step 1, for (4R, 1'R)- and (4R, 1'S)-2,2-dimethyl-4-[(5-fluoro-3 -benzylthiophenyl)methyloxymethyl]-1,3-dioxolane.

EXAMPLE 17

Preparation of (1S, 2R) and (1R,2R)-1-methyl-3-[(5-fluoro-3-(1,2-dihydro-1 -methyl-2-oxoquinoline-6-ylmethyloxy)phenyl)]-1,2,3-trimethoxypropane Step 1: (4R, 1'R)- and (4R, 1'S)-2,2-dimethyl-4-[(5-fluoro-3 -benzyloxyphenyl)hydroxymethyl]-1,3-dioxolane The desired compounds were prepared according to the method of Example 1, step 1, except substituting 5-fluoro-3-benzyloxybromobenzene, prepared as described in EPA 385 679, for 3-(napth-2-ylmethyloxy)-5-fluoro-bromobenzene.

Step 2: (4R)-2,2-dimethyl-4-[(5-fluoro-3-benzyloxyphenyl)oxomethyl]-1,3 -dioxolane The desired compound (98% yield) was prepared according to the method of Example 4, step 1, except substituting (4R, 1'R)- and (4R, 1'S)-2,2 -dimethyl-4-[(3benzyloxyphenyl)hydroxymethyl] -1,3-dioxolane for (4R, 1'R)- and (4R, 1'S)-2,2 -dimethyl-4-[(3-(napth-2-ylmethyloxy)phenyl)hydroxymethyl]-1,3-dioxolane.

Step 3: (4R, 1'R) and (4R, 1'S)-2,2-dimethyl-4-[1-(5-fluoro-3 -benzyloxyphenl)-1 -hydroxyethyl]-1,3-dioxolane To a solution of (4R)-2,2-dimethyl-4-[(5-fluoro-3 -benzyloxyphenyl))oxomethyl]-1,3-dioxolane (406 mg, 1.23 mmol) in freshly dried THF (10 mL) at ambient temperature was added a THF solution of methylmagnesiumbromide (410 μL, 3.0M solution, 1.23 mmol). After 1 hour the reaction appeared to be ~40% complete. Another portion of methylmagnesiumbromide (410 μL, 3.0M solution, 1.23 mmol) was added and the reaction stirred for 2 hours at ambient temperature, at which time it was judged to be complete by tlc. The reaction was quenched with excess saturated aqueous NH₄Cl and partitioned between ethyl acetate and H₂O. The layers were separated and the aqueous layer was extracted twice with ethyl acetate. The combined organic layers were washed with brine, dried over MgSO₄, filtered, and concentrated in vacuo to provide (4R, 1'R) and (4R, 1'S)-2,2-dimethyl-4-[1-(5-fluoro-3 -benzyloxyphenyl)-1 -hydroxyethyl]-1,3-dioxolane (340 mg, 980%) as a colorless oil which was carried on without purification.

Step 4: (4R, 1'R) and (4R, 1'S)-2,2-dimethyl-4-[1-(5-fluoro-3 -benzyloxyphenyl)-1 -methoxyethyl]-1,3-dioxolane The desired compounds were prepared according to the method of Example 1, step 2, except substituting (4R, 1'R) and (4R, 1'S)-2,2-dimethyl-4-[1-(5 -fluoro-3 -benzyloxyphenyl)-1-hydroxyethyl]-1,3-dioxolane (340 mg, 0.98 mmol), prepared as in step 3, for (4R, 1'S)-2,2-dimethyl-4-[(5-fluoro-3-(napth-2 -ylmethyloxy)phenyl)hydroxymethyl] -1,3-dioxolane. Pure (4R, 1'R) and (4R, 1'S)- 2,2-dimethyl-4-[1-(5-fluoro-3-benzyloxyphenyl)-1-methoxyethyl]-1,3-dioxolane (265 mg, 74%) were isolated by chromatography on silica gel (10% ethyl acetate:hexanes).

Step 5: (4R, 1'R) and (4R, 1'S)-2,2-dimethyl-4-[1-(3-hydroxy-5 -fluorophenyl)-1 -methoxyethyl]-1,3-dioxolane Hydrogenolysis was carried out as described in Example 5, step 1 except substituting (4R, 1'R) and (4R, 1'S)-2,2-dimethyl-4-[1-(5-fluoro-3 -benzyloxyphenyl)-1-methoxyethyl]-1,3-dioxolane (265 mg, 0.74 mmol), prepared as in step 4, for E-(4R)-O-Methyl-2,2-dimethyl-4-[(5-fluoro-3-(napth-2 -ylmethyloxy)phenyl)oximinomethyl] -1,3-dioxolane to provide the title compound (210 mg, 105%) as an oil.

Step 6: (4R, 1'R) and (4R, 1'S)-2,2-dimethyl-4-[1-(5-fluoro-3 -(1,2-dihydro-1 -methyl-2-oxoquinoline-6-ylmethyloxy)phenyl)-1-methoxyethyl]-1,3-dioxolane The desired compound was according to the method of Example 5, step 2, except substituting (4R, 1'R) and (4R, 1'S)-2,2-dimethyl-4-[1-(3-hydroxy-5 -fluorophenyl)-1-methoxyethyl]-1,3-dioxolane (265 mg, 0.74 mmol), prepared as in step 5, for E-(4R)-O-Methyl-2,2-dimethyl-4-[(5-fluoro-3-hydroxyphen-1 -yl)oximinomethyl] -1,3-dioxolane to provide (4R, 1'R) and (4R, 1'S)-2,2-dimethyl-4 -[1-(5-fluoro-3-(1,2-dihydro-1-methyl-2-oxoquinoline-6-ylmethyloxy)phenyl)-1 -methoxyethyl] -1,3-dioxolane (254 mg, 75%) as a colorless oil, after chromatography on silica gel (50% ethyl acetate: hexanes).

Step 7: (1S, 2R) and (1R,2R)-1-methyl-3-[(5-fluoro-3 -(1, 2-dihydro-1-methyl-2 -oxoquinoline-6-ylmethyloxy)phenyl)]-1,2,3-trimethoxypropane Deprotection to the diol and conversion to the corresponding trimethoxy product was carried out as described in Example 7, except substituting (4R, 1'R) and (4R, 1'S)-2,2-dimethyl-4-[1-(5-fluoro-3-(1,2-dihydro-1-methyl-2 -oxoquinoline-6 -ylmethyloxy)phenyl)-1-methoxyethyl]-1,3-dioxolane (104 mg, 0.23 mmol), prepared as in step 6, for anti-(4R, 1'S)-2,2-dimethyl-4-[(5-fluoro-3-(napth-2 -ylmethyloxy)phenyl)methyloxy)phenyl)methyloxymethyl]-1,3-dioxolane. Pure (1S, 2R or 1R,2S)-3 -methyl-3-[(5-fluoro-3-(1,2-dihydro-1-methyl-2-oxoquinoline-6 -ylmethyloxy)phenyl)]-1,2,3-trimethoxypropane, was isolated as a colorless oil (40 mg, 40%) by chromatography on silica gel (50% ethyl acetae:hexanes). $^1$H NMR (300 MHz, CDCl₃) δ 7.61–7.71 (3H, m), 7.41 (1H, d, J=9 Hz), 6.84 (1H, br s), 6.73–6.77 (2H, m), 6.63 (1H, dr, J=10.5, 3 Hz), 5.12

(2H, s), 3.75 (3H, s), 3.70 (1H, dd, J=11, 2 Hz), 3.42 (1H, dd, J=11, 8.5 Hz), 3.34 (3H, s), 3.27 (1H, dd, J=8.5, 2 Hz), 3.09 (3H, s), 3.06 (3H, s), 1.48 (3H, s). MS m/e 430 (M+H)$^+$, 458 (M+NH$_4$)$^+$.

Analysis calc'd for $C_{24}H_{28}NO_5F$: C, 67.12; H, 6.57; N, 3.26. Found: C, 66.89; H, 6.56; N, 3.08.

EXAMPLE 18

Preparation of E-(4R)-O-Methyl-2,2-dimethyl-4-[(5-fluoro-3-(1,2-dihydro-1-methyl- 2-oxoquinoline-6-ylmethyloxy)phenyl)oximinomethyl]-1,3-dioxolane
Step 1: (S)-(–)-2,2-dimethyl-1,3-dioxolane-4-carboxaldehyde The desired compound was prepared as described in Jackson, *Synthetic Commun.* 1988, 18(4), 337–341), except starting with L-(S)-glyceraldehyde, prepared as described by Hubschwerlen, C. *Synthesis*, 1986, 962–964, instead of D-(R)-glyceraldehyde.
Step 2: (4S, 1'R)- and (4S, 1'S)-2,2-dimethyl-4-[(5-fluoro-3-(napth-2 -ylmethyloxy)phenyl)hydroxymethyl]-1,3-dioxolane The desired compound was prepared according to the method of Example 1, step 1, except substituting (S)-(–)-2, 2-dimethyl-1,3-dioxolane-4-carboxaldehyde, prepared as in step 1, for (R)-(+)-2,2-dimethyl-1,3-dioxolane-4-carboxaldehyde.
Step 3: Z- and E-(4R)-O-methyl-2,2-dimethyl-4-[(5-fluoro-3-(napth-2 -ylmethyloxy)phenyl)oximinomethyl]-1,3-dioxolane The desired compound was prepared according to the method of Example 4, except substituting (4S, 1'R)- and (4S, 1'S)-2,2-dimethyl-4-[(5-fluoro-3-(napth-2 -ylmethyloxy)phenyl)hydroxymethyl]-1,3-dioxolane, prepared as in step 2, for (4R, 1'R)- and (4R, 1'S)-2,2-dimethyl-4-[(5-fluoro-3-(napth-2 -ylmethyloxy)phenyl)hydroxymethyl]-1,3-dioxolane.
Step 4: E-(4R)-O-methyl-2,2-dimethyl-4-[(5-fluoro-3-(2,2-dihydro-1-methyl-2-oxoquinoline-6-ylmethyloxy)phenyl)oximinomethyl]-1,3-dioxolane The desired compound was prepared according to the method of Example 5, except substituting E-(4R)-O-methyl-2,2-dimethyl -4-[(5-fluoro-3-hydroxyphen-1 -yl)oximinomethyl]-1,3-dioxolane, prepared as in step 3, for E-(4S)-O-Methyl-2,2 -dimethyl-4-[(5-fluoro-3-hydroxyphen-1-yl)oximinomethyl]-1,3-dioxolane. $^1$H NMR (300 MHz, CDCl$_3$) δ 7.68 (1H, d, J=9 Hz), 7.59–7.63 (2H, m), 7.39 (1H, d, J=9 Hz), 6.82 (1H, br s), 6.68–6.77 (4H, m), 5.10 (2H, s), 4.86 (1H, t, J=7.5 Hz), 4.13 (1H, dd, J=8.5, 7.5 Hz), 3.92 (1H, d, J=8.5, 7.5 Hz), 3.87 (3H, s), 3.74 (3H, s), 1.38 (3H, s), 1.30 (3H, s). MS m/e 441 (M+H)$^+$, 458 (M+NH$_4$)$^+$.

Analysis calc'd for $C_{24}H_{25}N_2O_5F$: C, 65.44; H, 5.72; N, 6.36. Found: C, 65.28; H, 5.83; N, 6.12.

EXAMPLE 19

Preparation of Z-(4R)-O-methyl-2,2-dimethyl-4-[(5-fluoro-3-(1,2-dihydro-1-methyl- 2-oxoquinoline-6-ylmethyloxy)phenyl)oximinomethyl]-1,3-dioxolane The title compound was prepared as described in Example 18 except that Z-( 4R)-O-methyl-2,2-dimethyl-4-[(5-fluoro-3-hydroxyphen-1-yl)oximinomethyl]-1,3-dioxolane was substituted for E-(4S)-O-Methyl-5-fluoro-3 -hydroxyphenyl)oximinomethyl]-1,3-dioxolane. $^1$H NMR (300 MHz, CDCl$_3$) δ 7.68 (1H, d, J=9 Hz), 7.59–7.63 (2H, m), 7.39 (1H, d, J=9 Hz), 7.02 (1H, br s 6.94 (1H, ddd, J=9, 3, 1.5 Hz), 6.74 (1H, d, J=10.5Hz), 6.72 (1H, dt, J=10.5, 3, 3 Hz), 5.47 (1H, t, J=7.5 Hz), 5.12 (2H, s), 4.45 (1H, dd, J=8.5, 7.5 Hz), 3.97 (3H, s), 3.84 (1H, dd, J=8.5, 7.5 Hz), 3.74 (3H, s), 1.38 (3H, s), 1.31 (3H, s) . MS m/e 441 (M+H)$^+$, 458 (M+NH$_4$)$^+$.

Analysis calc'd for $C_{24}H_{25}N_2O_5F$: C, 65.44; H, 5.72; N, 6.36. Found: C, 65.28; H, 5.75; N, 6.38.

EXAMPLE 20

Preparation of E- and Z-(4R)-O-ethyl-2,2-dimethyl-4-[(5-fluoro-3-(1,2-dihydro-1 -methyl-2-oxoquinoline-6-ylmethyloxy)phenyl)oximinomethyl]-1,3-dioxolane The title compound was prepared as described in Example 18 except substituting O-ethylhydroxylamine hydrochloride for O-methylhydroxylamine hydrochloride. The title compound was purified by chromatography on silica gel (75% ethyl acetate:hexanes) to provide a 1:2 mixture of the E:Z isomers as a colorless oil. The $^1$H NMR spectrum is reported for a 1:2 E:Z mixture, where possible the chemical shifts for the same protons will be noted as being E or Z. $^1$H NMR (300 MHz, CDCl$_3$). δ 7.60–69 (3H, m), 7.39 (1H, d, J=9 Hz), 6.67–7.03 (4H, m), 5.47(Z) and 4.37(E) (1H, t, J=7.5 Hz), 5.12(Z) and 4.99(E) (2H, s), 4.47(Z) (0.66 H, dd, J=8, 7.5 Hz), 4.08–4.25 (2.66 H, m), 3.84(Z) and 3.93(Z) (1H, dd, J= 8.5, 7.5 Hz), 3.74 (3H, s), 1.20–1.40 (9H, m). MS m/e 455 (M+H)$^+$, 472 (M+NH$_4$)$^+$.

Analysis calc'd for $C_{25}H_{27}N_2O_5F(0.25\ H_2O)$: C, 65.42; H, 6.04; N, 6.10. Found: C, 65.59; H, 6.06; N, 5.92.

EXAMPLE 21

Preparation of E- and Z-(4S)-2,2-dimethyl-4-[(5-fluoro-3-(1,2-dihydro-1-methyl-2 -oxoquinoline-6-ylmethyloxy)phenyl)oximinomethyl]-1,3-dioxolane The title compound was prepared as described in Example 18, except that hydroxylamine hydrochloride was used instead of O-methylhydroxylamine hydrochloride. The title compound was purified by chromatography on silica gel (50% ethyl acetate:hexanes) to provide a 2:3 mixture of the E:Z isomers as a colorless solid. The $^1$H MR spectrum is reported for a 2:3 E:Z mixture, where possible the chemical shifts for the same protons will be noted as being E or Z. mp 156°–160° C. $^1$H NMR (300 MHz, CDCl$_3$) δ 7.60–69 (3H, m), 7.39 (1H, d, J=9 Hz), 6.70–7.01 (4H, m), 5.57(Z) and 4.39(E) (1H, t, J=7.5 Hz), 5.12(Z) and 5.11(E) (2H, s), 4.49(Z) and 4.14(E) (1H, dd, J=8, 7.5 Hz), 3.92(Z) and 3.96(E) (1H, dd, J=8, 6.5 Hz), 3.74 (3H, s), 1.39 (3H, s), 1.32 (3H, s). MS m/e 427 (M+H)$^+$, 444 (M+NH$_4$)$^+$.

Analysis calc'd for $C_{23}H_{23}N_2O_5F(0.25\ H_2O)$: C, 64.10; H, 5.50; N, 6.50. Found: C, 64.14; H, 5.47; N, 6.17.

EXAMPLE 22

Preparation of E-(4S, 2R) and (4S, 2S)-2-methoxy-O-methyl-4-[(5-fluoro-3-(1,2 -dihydro-1-methyl-2-oxoquinoline-6-ylmethyloxy)phenyl)oximinomethyl]-1,3 -dioxolane
Step 1: E-O-methyl-(4S)-2,2-dimethyl-4-(5-fluoro-3 -(benzyloxyphenyl)oximinomethyl]-1,3-dioxolane The desired compound was prepared according to the method of Example 4, except substituting 3-benzyloxy-5-fluorobromobenzene, prepared as described in EPA 385 679 for 3-(napth-2-ylmethyloxy)-5-fluorobromobenzene.
Step 2: E-O-methyl-(4S)-1-[(5-fluoro-3-benzyloxyphenyl)oximinomethyl]-1,2 -dihydroxyethane The desired compound was prepared according to the method of Example 2, step 1, except substituting E-O-methyl-(4R) -2,2-dimethyl-4-[(5-fluoro-3 -benzyloxyphenyl)oximinomethyl]-1,3-dioxolane, prepared as in step 1, for anti-(4R, 1'S)-2,2-dimethyl-4-[(5-fluoro-3-(napth-2-ylmethyloxyphenyl)methyloxymethyl] -1,3-dioxolane.

Step 3: E-O-methyl-(4S, 2R) and (4S, 2S)-2-methoxy-4-[(5-fluoro-3-benzyloxyphenyl)oximinomethyl]-1,3-dioxolane To a solution of E-O-methyl-(4S)-1-[(5-fluoro-3-(benzyloxyphenyl)oximinomethyl]-1,2-dihydroxyethane (217 mg, 0.68 mmol), prepared as in step 2, in DMF was added trimethylorthoformate (743 µL, 6.8 mmol) and trimethylsilyl chloride (170 µL, 1.36 mmol). The resulting mixture was stirred at ambient temperature for 20 min and partitioned between saturated aqueous NH₄Cl and ethyl acetate. The layers were separated and the aqueous layer was extracted twice with ethyl acetate. The combined organic layers were washed with brine, dried over MgSO₄, filtered, and concentrated in vacuo to provide E-O-methyl-(4S, 2R) and (4S, 2S)-2-methoxy-4-[(5-fluoro-3-benzyloxyphenyl)oximinomethyl]-1,3-dioxolane (269 mg, 110%) as a colorless oil which was carried on without purification.

Step 4: E-(4S, 2R) and (4S, 2S)-O-methyl-2-methoxy-4-[(5-fluoro-3-((1,2-dihydro-1-methyl-2-oxoquinoline-6-yl)methoxy)phenyl)oximinomethyl]-1,3-dioxolane The desired compound was prepared according to the method of Example 5, except substituting E-O-methyl-(4S, 2R) and (4S, 2S)-2-methoxy-4-[(5-fluoro-3-benzyloxyphenyl)oximinomethyl]-1,3-dioxolane, prepared as in step 3, for E-(4S)-O-methyl- 2,2-dimethyl-4-[(5-fluoro-3-(napth-2-yl-methyloxy)phenyl)oximinomethyl] -1,3-dioxolane. Chromatography on silica gel (50% ethyl acetate:hexanes) provided a 1:2 syn::anti mixture of the title compounds (31%) as an oil. $^1$H NMR (500 MHz, DMSO-D$_6$) δ 7.92 (1H, d, J=10 Hz), 7.82 (1H, d, J=2.5 Hz), 7.71 (1H, dd, J= 10, 2.5 Hz), 7.56 (1H, d, J=10 Hz), 6.99 (1H, dr, J=10, 2.5 Hz), 6.89 and 6.83 (1H, br s), 6.81 and 6.77 (1H, br d, J=9 Hz), 6.63 (1H, d, J=10 Hz), 5.70 and 5.78 (1H, s), 5.20 (2H, s), 5.11 and 5.02 (1H, dd and t, J=6, 4 and 7.5 Hz), 3.98– 4.17 (2H, m), 3.77 and 3.78 (3H, s), 3.63 (3H, s), 3.17 and 3.04 (3H, s). MS m/e 441 (M+H)$^+$, 458 (M+NH$_4$)$^+$.

Analysis calc'd for C$_{23}$H$_{23}$N$_2$O$_6$F: C, 62.44; H, 5.24; N, 6.33. Found: C, 62.41; H, 5.17; N, 6.30.

The compounds represented in Table 2 are prepared by alkylation of Z and E-( 4S) -O-Methyl-2,2-dimethyl-4-[(5-fluoro-3-hydroxyphen-1-yl)oximinomethyl]-1,3 -dioxolane, or syn-(4R, 1'R)- and anti-(4R, 1'S)-2,2-dimethyl-4-[(5-fluoro-3-(napth- 2-ylmethyloxy)phenyl)methyloxymethyl]-1,3-dioxolane, with the requisite 3 -heteroaryl-prop-2-yn-yl halide which was prepared as described in the patent literature (EPA 385 663, Crawley, G. C.).

TABLE 2

Novel Aryl- and Heteroarylacetylene Substituted Dioxolanes

| Example | Ar¹ | L² |
|---|---|---|
| 23 | pyrid-2-yl | >C=NOCH₃ |
| 24 | pyrid-2-yl | >CHOCH₃ |
| 25 | pyrid-3-yl | >C=NOCH₃ |
| 26 | pyrid-3-yl | >CHOCH₃ |
| 27 | pyrid-4-yl | >C=NOCH₃ |
| 28 | pyrid-4-yl | >CHOCH₃ |
| 29 | fur-2-yl | >C=NOCH₃ |
| 30 | fur-2-yl | >CHOCH₃ |
| 31 | fur-3-yl | >C=NOCH₃ |

TABLE 2-continued

Novel Aryl- and Heteroarylacetylene Substituted Dioxolanes

| Example | Ar¹ | L² |
|---|---|---|
| 32 | fur-3-yl | >CHOCH₃ |
| 33 | thien-2-yl | >C=NOCH₃ |
| 34 | thien-2-yl | >CHOCH₃ |
| 35 | thien-3-yl | >C=NOCH₃ |
| 36 | thien-3-yl | >CHOCH₃ |
| 37 | benzo[b]thien-2-yl | >C=NOCH₃ |
| 38 | benzo[b]thien-2-yl | >CHOCH₃ |
| 39 | benzo[b]fur-2-yl | >C=NOCH₃ |
| 40 | benzo[b]fur-2-yl | >CHOCH₃ |
| 41 | thiazo-2-yl | >C=NOCH₃ |
| 42 | thiazo-2-yl | >CHOCH₃ |
| 43 | imidazol-2-yl | >C=NOCH₃ |
| 44 | imidazol-2-yl | >CHOCH₃ |
| 45 | pyrimid-2-yl | >C=NOCH₃ |
| 46 | pyrimid-2-yl | >CHOCH₃ |

The compounds represented in Table 3 are prepared by alkylation of Z- and E-( 1S )-O-methyl-1-[(5-fluoro-3-hydroxyphenyl)oximinomethyl]1,2-dimethoxyethane or (1S, 2R)-1-(5-fluoro-3-hydroxyphenyl)-1,2,3-trimethoxypropane with the requisite 3-heteroaryl-prop-2-yn-yl halide which was prepared as described in the patent literature (EPA 385 663, Crawley, G. C.).

TABLE 3

Novel Aryl- and Heteroarylacetylene Substituted Diethers

| Example | Ar¹ | L² |
|---|---|---|
| 47 | pyrid-2-yl | >C=NOCH₃ |
| 48 | pyrid-2-yl | >CHOCH₃ |
| 49 | pyrid-3-yl | >C=NOCH₃ |
| 50 | pyrid-3-yl | >CHOCH₃ |
| 51 | pyrid-4-yl | >C=NOCH₃ |
| 52 | pyrid-4-yl | >CHOCH₃ |
| 53 | fur-2-yl | >C=NOCH₃ |
| 54 | fur-2-yl | >CHOCH₃ |
| 55 | fur-3-yl | >C=NOCH₃ |
| 56 | fur-3-yl | >CHOCH₃ |
| 57 | thien-2-yl | >C=NOCH₃ |
| 58 | thien-2-yl | >CHOCH₃ |
| 59 | thien-3-yl | >C=NOCH₃ |
| 36 | thien-3-yl | >CHOCH₃ |
| 60 | benzo[b]thien-2-yl | >C=NOCH₃ |
| 61 | benzo[b]thien-2-yl | >CHOCH₃ |
| 62 | benzo[b]fur-2-yl | >C=NOCH₃ |
| 63 | benzo[b]fur-2-yl | >CHOCH₃ |
| 64 | thiazo-2-yl | >C=NOCH₃ |
| 65 | thiazo-2-yl | >CHOCH₃ |
| 66 | imidazol-2-yl | >C=NOCH₃ |
| 67 | imidazol-2-yl | >CHOCH₃ |
| 68 | pyrimid-2-yl | >C=NOCH₃ |

TABLE 3-continued

Novel Aryl- and Heteroarylacetylene Substituted Diethers

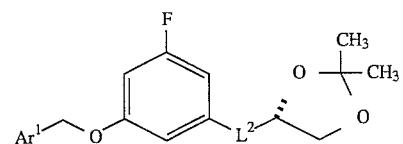

| Example | Ar¹ | L² |
|---|---|---|
| 69 | pyrimid-2-yl | >CHOCH₃ |

The compounds represented in Table 4 are prepared by alkylation of Z- and E-( 1S)-O-methyl-1-[(5-fluoro-3-hydroxyphenyl)oximinomethyl]-1,2-dimethoxyethane or (1S, 2R)-1-(5-fluoro-3-hydroxyphenyl)-1,2,3-trimethoxypropane with the requisite arylmethyl halide as described in Example 5.

TABLE 4

Novel Heteroarylmethyloxy Substituted Diethers

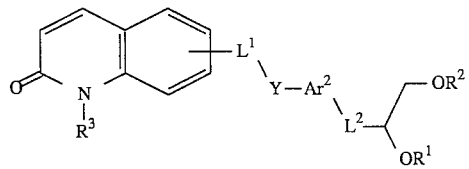

| Example | Ar¹ | L² |
|---|---|---|
| 70 | quinoxalin-6-yl | >C=NOCH₃ |
| 71 | quinoxalin-6-yl | >CHOCH₃ |
| 72 | quinolin-6-yl | >C=NOCH₃ |
| 73 | quinolin-6-yl | >CHOCH₃ |
| 74 | 1-methyl-2-oxo-1,2,3,4-tetrahydroquinolin-6-yl | >C=NOCH₃ |
| 75 | 1-methyl-2-oxo-1,2,3,4-tetrahydroquinolin-6-yl | >CHOCH₃ |
| 76 | 4-methyl-3-oxo-3,4-dihydrobenzoxazin-7-yl | >C=NOCH₃ |
| 77 | 4-methyl-3-oxo-3,4-dihydrobenzoxazin-7-yl | >CHOCH₃ |
| 78 | 2,2,4-trimethyl-3-oxo-2,3-dihydro-4H-1,4-benzoxazin-7-yl | >C=NOCH₃ |
| 79 | 2,2,4-trimethyl-3-oxo-2,3-dihydro-4H-1,4-benzoxazin-7-yl | >CHOCH₃ |
| 80 | 1,3-dimethyl-2-oxo-2,3-dihydrobenzimidazol-5-yl | >C=NOCH₃ |
| 81 | 1,3-dimethyl-2-oxo-2,3-dihydrobenzimidazol-5-yl | >CHOCH₃ |

The compounds represented in Table 5 are prepared by alkylation of Z and E-( 4S)-O-methyl-2,2-dimethyl-4-[(5-fluoro-3-hydroxyphen-1-yl)oximinomethyl]-1,3-dioxolane, or syn-(4R, 1'R)- and anti-(4R, 1'S)-2,2-dimethyl-4-[(5-fluoro-3-(napth- 2-ylmethyloxy)phenyl)methyloxymethyl]-1,3-dioxolane with the requisite arylmethyl halide as described in Example 5.

TABLE 5

Novel Heteroarylmethyloxy Substituted Dioxolanes

| Example | Ar¹ | L² |
|---|---|---|
| 82 | quinoxalin-6-yl | >C=NOCH₃ |
| 83 | quinoxalin-6-yl | >CHOCH₃ |
| 84 | quinolin-6-yl | >C=NOCH₃ |
| 85 | quinolin-6-yl | >CHOCH₃ |
| 86 | 1-methyl-2-oxo-1,2,3,4-tetrahydroquinolin-6-yl | >C=NOCH₃ |
| 87 | 1-methyl-2-oxo-1,2,3,4-tetrahydroquinolin-6-yl | >CHOCH₃ |
| 88 | 4-methyl-3-oxo-3,4-dihydrobenzoxazin-7-yl | >C=NOCH₃ |
| 89 | 4-methyl-3-oxo-3,4-dihydrobenzoxazin-7-yl | >CHOCH₃ |
| 90 | 2,2,4-trimethyl-3-oxo-2,3-dihydro-4H-1,4-benzoxazin-7-yl | >C=NOCH₃ |
| 91 | 2,2,4-trimethyl-3-oxo-2,3-dihydro-4H-1,4-benzoxazin-7-yl | >CHOCH₃ |
| 92 | 1,3-dimethyl-2-oxo-2,3-dihydrobenzimidazol-5-yl | >C=NOCH₃ |
| 93 | 1,3-dimethyl-2-oxo-2,3-dihydrobenzimidazol-5-yl | >CHOCH₃ |

We claim:

1. A compound having the structure

or a pharmaceutically acceptable salt thereof wherein $R^3$ is hydrogen or alkyl of one to four carbon atoms;

$L^1$ is a valence bond or is selected from alkylene of one to three carbon atoms, propenylene, and propynylene;

Y is selected from the group consisting of oxygen,
>$NR^5$ wherein $R^5$ is hydrogen or alkyl of one to four carbon atoms, and $$\overset{(O)_n}{\underset{|}{-S-}}$$

where n=0, 1, or 2;

$Ar^2$ is phenyl, optionally substituted with one or more substituents selected from the group consisting of
 alkyl of one to four carbon atoms,
 alkoxy of one to four carbon atoms,
 haloalkyl,
 halogen,
 cyano,
 amino,
 alkoxycarbonyl of one to four carbon atoms, and
 dialkylaminocarbonyl where the alkyl portions are each independently of one to four carbon atoms;

$L^2$ is selected from the group consisting of (a)

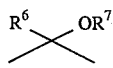

wherein $R^6$ is hydrogen or alkyl of one to four carbon atoms,
and $R^7$ is alkyl of one to four carbon atoms, and (b)

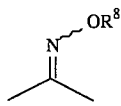

wherein $R^8$ is hydrogen or alkyl of one to four carbon atoms; and $R^1$ and $R^2$ are alkyl of one to four carbon atoms, or taken together with the oxygen atoms to which they are attached, form a ring of the structure

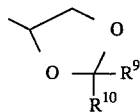

wherein $R^9$ and $R^{10}$ are independently selected from the group consisting of
hydrogen,
alkyl of one to four carbon atoms,
alkoxy of one to four carbon atoms, and
haloalkyl of one to four carbon atoms.

2. A compound or pharmaceutically acceptable salt thereof as defined by claim 1
wherein $L^2$ is

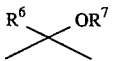

wherein $R^6$ is hydrogen or alkyl of one to four carbon atoms,
and $R^7$ is alkyl of one to four carbon atoms, and 3. A compound or pharmaceutically acceptable salt thereof as defined by claim 2
wherein $R^1$ and $R^2$ are alkyl of one to four carbon atoms.

4. A compound or pharmaceutically acceptable salt thereof as defined by claim 2
wherein $R^1$ and $R^2$ are taken together with the oxygen atoms to which they are attached, form a ring of the structure

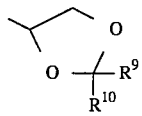

wherein $R^9$ and $R^{10}$ are independently hydrogen or alkyl of one to four carbon atoms.

5. A compound or pharmaceutically acceptable salt thereof as defined by claim 1 selected from the group consisting of E-(4S)-O-methyl-2,2-dimethyl-4-[(5-fluoro-3-(1,2-dihydro-1-methyl-2-oxoquinoline-6-ylmethyloxy)phenyl)oximinomethyl]-1,3-dioxolane, Z-(4S)-O-methyl-2,2-dimethyl-4-[(5-fluoro-3-(1,2-dihydro-1-methyl-2-oxoquinoline-6-ylmethyloxy)phenyl)oximinomethyl]-1,3-dioxolane, E-(4R)-O-methyl-2,2-dimethyl-4-[(5-fluoro-3-(1,2-dihydro-1-methyl-2-oxoquinoline-6-ylmethyloxy)phenyl)oximinomethyl]-1,3-dioxolane, Z-(4R)-O-methyl-2,2-dimethyl-4-[(5-fluoro-3-(1,2-dihydro-1-methyl-2-oxoquinoline-6-ylmethyloxy)phenyl)oximinomethyl]-1,3-dioxolane, Z-(4R)-O-ethyl-2,2-dimethyl-4-[(5-fluoro-3-(1,2-dihydro-1-methyl-2-oxoquinoline-6-ylmethyloxy)phenyl)oximinomethyl]-1,3-dioxolane, and E-(4R)-O-ethyl-2,2-dimethyl-4-[(5-fluoro-3-(1,2-dihydro-1-methyl-2-oxoquinoline-6-ylmethyloxy)phenyl)oximinomethyl]-1,3-dioxolane.

6. A pharmaceutical composition for inhibiting the biosynthesis of leukotrienes comprising a therapeutically effective amount of a compound as defined by claim 1 in combination with a pharmaceutically acceptable carrier.

7. A method of inhibiting the biosynthesis of leukotrienes comprising administering to a mammal in need of such treatment a therapeutically effective amount of a compound as defined by claim 1.

* * * * *